(12) United States Patent
Kingma et al.

(10) Patent No.: US 11,813,107 B2
(45) Date of Patent: Nov. 14, 2023

(54) MEDICAL IMAGING SYSTEM

(71) Applicant: RADuxtion, LLC, Fishers, IN (US)

(72) Inventors: Phillip R. Kingma, Fishers, IN (US); Letrisha Weber, Indianapolis, IN (US)

(73) Assignee: RADuxtion, LLC, Fishers, IN (US)

( * ) Notice: Subject to any disclaimer, the term of this patent is extended or adjusted under 35 U.S.C. 154(b) by 456 days.

(21) Appl. No.: 17/161,762

(22) Filed: Jan. 29, 2021

(65) Prior Publication Data
US 2022/0240883 A1 Aug. 4, 2022

(51) Int. Cl.
| | | |
|---|---|---|
| *A61B 6/00* | (2006.01) | |
| *G16H 40/67* | (2018.01) | |
| *G16H 10/60* | (2018.01) | |
| *G16H 30/20* | (2018.01) | |
| *G16H 40/40* | (2018.01) | |

(Continued)

(52) U.S. Cl.
CPC ............ *A61B 6/542* (2013.01); *A61B 6/4494* (2013.01); *A61B 6/545* (2013.01); *A61B 6/548* (2013.01); *A61B 6/56* (2013.01); *A61B 6/566* (2013.01); *G16H 10/60* (2018.01); *G16H 30/20* (2018.01); *G16H 40/40* (2018.01); *G16H 40/67* (2018.01); *G16H 70/20* (2018.01); *A61B 6/03* (2013.01); *A61B 6/4441* (2013.01); *A61B 6/487* (2013.01); *A61B 6/544* (2013.01); *A61B 6/563* (2013.01)

(58) Field of Classification Search
CPC ....... A61B 6/03; A61B 6/4441; A61B 6/4494; A61B 6/487; A61B 6/542; A61B 6/544; A61B 6/545; A61B 6/548; A61B 6/56; A61B 6/563; A61B 6/566; G16H 10/60; G16H 30/20; G16H 40/40; G16H 40/67
See application file for complete search history.

(56) References Cited

U.S. PATENT DOCUMENTS

| 5,293,415 A | 3/1994 | Hartley et al. |
| 7,490,987 B2 | 2/2009 | Busch |

(Continued)

FOREIGN PATENT DOCUMENTS

| EP | 3367900 A1 | 9/2018 |
| EP | 2491506 B1 | 12/2019 |
| JP | 2009042247 A | 2/2009 |

OTHER PUBLICATIONS

Hernanz-Schulman et al., Pause and Pulse: ten Steps That Help Manage Radiation Dose during Pediatric Fluoroscopy, Pediatric Imaging.Review, Aug. 2011 pp. 475-481.

(Continued)

*Primary Examiner* — Mark R Gaworecki
(74) *Attorney, Agent, or Firm* — Banner & Witcoff, Ltd.

(57) ABSTRACT

A radiation reduction system that includes control logic for controlling an imaging device that is configured to provide an image of a subject during a medical procedure using electromagnetic radiation. The control logic automatically determines operating settings useful to generate one or more medically useful images of the subject while significantly reducing the overall radiation exposure to the subject and/or nearby personnel. The settings are determined based on factors such as age, body type, gender, and the like. The control logic may be in the imaging device, in a nearby computer such as a table or smart phone in communication with the imaging device, or in a remote server communicating with the imaging device directly, or via another computer.

20 Claims, 9 Drawing Sheets

(51) Int. Cl.
*G16H 70/20* (2018.01)
*A61B 6/03* (2006.01)

(56) References Cited

U.S. PATENT DOCUMENTS

| | | |
|---|---|---|
| 7,620,142 B1 | 11/2009 | Toth |
| 7,949,098 B2 | 5/2011 | Ellinwood et al. |
| 8,903,037 B2 | 12/2014 | Yu et al. |
| 9,275,189 B2 | 3/2016 | Walker et al. |
| 9,323,896 B2 | 4/2016 | Falt et al. |
| 9,592,022 B2 | 3/2017 | Larson |
| 10,085,698 B2 | 10/2018 | Fan et al. |
| 2004/0131141 A1 | 7/2004 | Horiuchi |
| 2007/0076842 A1 | 4/2007 | Tkaczyk et al. |
| 2010/0091950 A1 | 4/2010 | Ellinwood et al. |
| 2019/0099148 A1 | 4/2019 | Rupcich et al. |
| 2019/0108905 A1 | 4/2019 | Zhang et al. |
| 2021/0137482 A1* | 5/2021 | Bernhardt .............. G16H 30/20 |
| 2021/0267564 A1 | 9/2021 | Brody |

OTHER PUBLICATIONS

Mahesh, Imaging & Therapeutic Technology, Fluoroscopy: Patient Radiation Exposure Issues, Radiographics, Jul. 2001, vol. 21, Issue 4.

Agnew, C., et al. (2021). Optimisation of Varian TrueBeam head, thorax and pelvis CBCT based on patient size. Journal of Radiotherapy in Practice, 20(3), 248-256. doi:10.1017/S1460396920000618.

Ketelsen et al., Automated Corrupted Tomography Dose-Saving Algorithm to Protect Radiosensitive Tissues Estimation of Radiation Exposure and Image Quality Considerations; Investigative Radiology 47(2)p. 148-152 Feb. 2012.

Yu et al., Automatic selection of tube potential for radiation dose reduction in CT: a general strategy; Jan. 2010 Med Phys. 37(1): 234-43.

* cited by examiner

MEDICAL IMAGING SYSTEM

COPYRIGHT NOTICE

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

BACKGROUND

Medical imaging includes a variety of techniques that may be used to create a visual representation of the internal structures of the human body, animals or other inanimate objects. Such techniques may be helpful for evaluating content, orientation, integrity or for diagnosing and treating medical issues.

However, some forms of imaging may require the use of radiation to provide an image of the body or subject or material by exposing not only the patient or subject, but also the personnel performing the imaging procedure to radiation. Extended exposure to radiation may cause adverse effects and increased risk of conditions such as cataracts and cancer, including but not limited to cancers of the thyroid, breast, lymphoma, leukemia, glioblastomas and radiation injuries.

Radiation safety practices are generally determined based on radiation exposure which is a function of duration of exposure (time), distance from source of radiation, dose to the patient and scatter radiation to the personnel (also referred to herein as "scatter rate" or "rate of scatter"). For example, a typical imaging system may create radiation for 0.9 to 1.2 secs or more, with scatter radiation detectable to 6 feet and as much as 10 feet. This creates a typical scatter rate of over 300 milliroentgen per hour (mR/hr) or more—for every image generated during a given imaging session.

In most imaging systems, the imaging device automatically determines operating settings by exposing the subject at a given setting and automatically evaluating the resulting image. The subject is then immediately re-exposed at a modified setting and the image is automatically re-evaluated again. This exposure cycle is repeated multiple times, rapidly and automatically, within the typical 0.9 to 1.2 seconds, until an optimal image is produced. This process occurs seamlessly and fluidly, but yet not obvious to the operating personnel, every time an exposure button is depressed. Thus the overall radiation exposure is affected by the increased exposure cycle, for a second or more to the patient and anyone standing nearby.

This feature is frequently referred to as Automatic Exposure Control (e.g. AEC). Although generally effective, AEC significantly increases the overall radiation exposure time and dose for the subject. More importantly, it significantly increases the amount of radiation delivered to personnel performing the imaging procedure. While the subject may only experience occasional exposure over the course of a lifetime, the clinical personnel involved may experience multiple exposures day after day for many years.

SUMMARY

Disclosed is an imaging system, and method of operation for such a system, that reduces or eliminates high doses of harmful radiation. The disclosed system limits radiation exposure to individuals nearby such as clinical personnel, staff, and the patient during the imaging process. In one example, the system includes a medical imaging device configured to capture an image of a patient or subject during a medical procedure using electromagnetic radiation such as x-rays for example. In another aspect, the system may include one or more computers in communication with the imaging device. One of these computers may, for example, be configured to generate and/or display a user interface that is configured to accept input that optionally includes, but is not limited to, information identifying the imaging device (e.g. the manufacturer, model number or other identifying information), a specific type of imaging procedure to be performed by the imaging device in conjunction with the medical procedure, a targeted location of the anatomy of the patient or subject which is to be imaged by the imaging device, and/or physical characteristics of the subject that include gender, body type, weight or other relevant characteristics.

In another aspect, the computer may use the specific type of imaging procedure to be performed, the target location of the anatomy of the subject and the physical characteristics of the subject to calculate operating settings of the imaging device which optionally include any combination of kilovoltage peak (kVp), tube current and exposure time (mAs) and any other relevant machine settings. The operating setting may be transmitted from the computer to the imaging device using a communication link electrically connecting the computer to the imaging device thus allowing the computer to control the imaging device to generate an image of the subject using the calculated operating settings to reduce overall radiation exposure.

In another aspect, the controller or computer in communication with the imaging device is operable to deactivate Automatic Exposure Control (AEC) which is an imaging feature whereby the imaging device automatically adjusts or compensates for subject variability by applying multiple doses of radiation with different settings to utilize multiple exposures to produce a single optimal image.

In another aspect, the system of the present disclosure is operable to obtain a usable image while limiting the scatter rate to less than 300 mR/hr, less than 200 mR/hr, or less than 100 mR/hr per image.

In another aspect, a system of the present disclosure is operable to reduce or eliminate the range of scatter radiation to less than 10 feet, less than 6 feet, or less than 4 feet while still producing a usable image.

In another aspect, the system of the present disclosure is operable to reduce the duration of scatter radiation production to less than 0.5 secs, less than 0.35 secs, or less than 0.2 seconds for a single usable image.

Further forms, objects, features, aspects, benefits, advantages, and examples of the concepts summarized above are described in further detail in the description, claims, and drawings.

DETAILED DESCRIPTION

Figure 1:
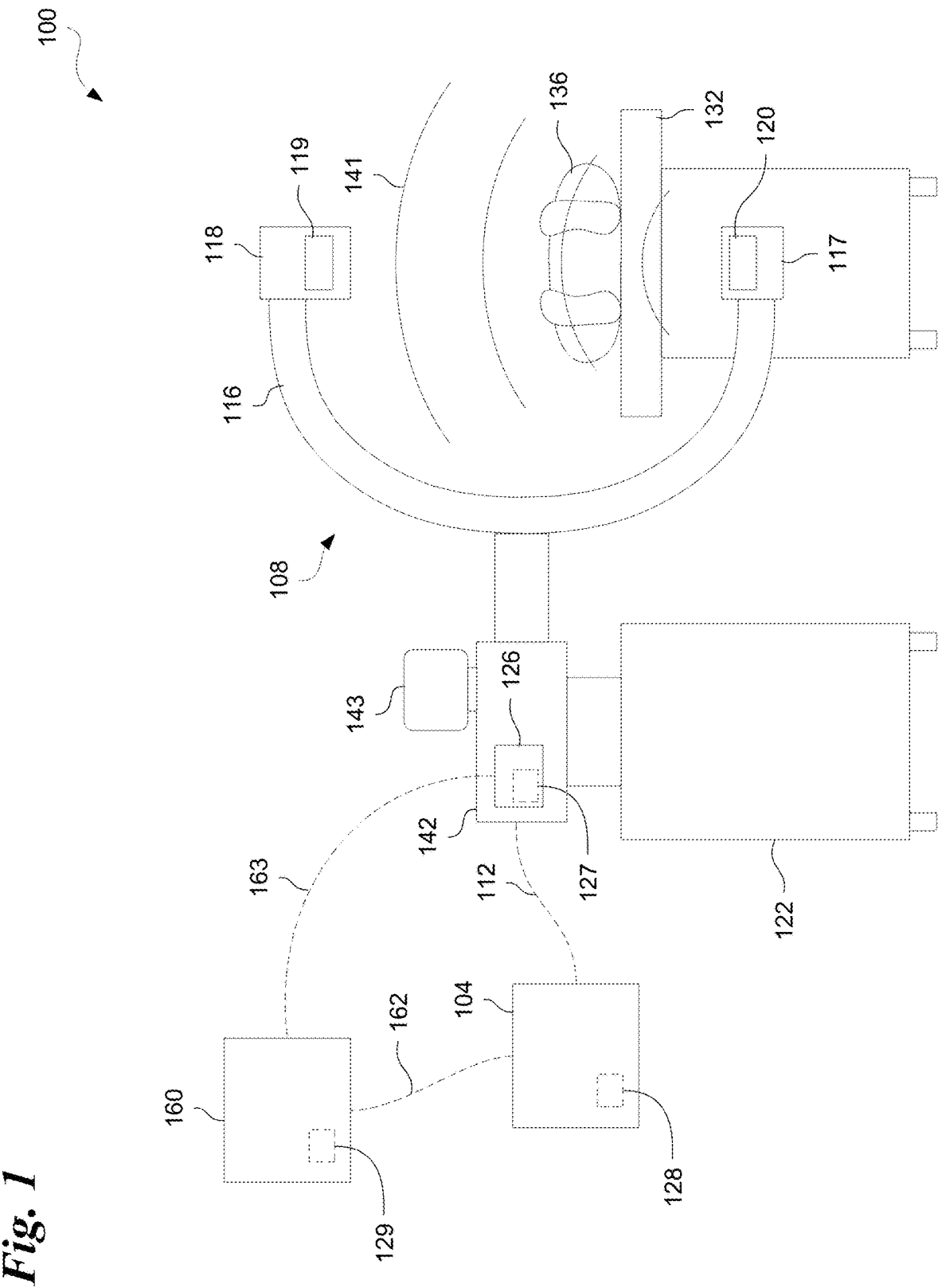
FIG. 1 illustrates components of one example of a radiation reduction system of the present disclosure.

FIG. 1 illustrates at 100 one example of components that may be included in the disclosed imaging system for reducing radiation. The system 100 optionally includes a computer 104 coupled to an imaging device 108 via an optional communication link 112. The communication link 112 may be of any suitable type, such as a wired connection between the computer 104 and the imaging device that uses coaxial cable, fiber optic cable, and the like. In another example, the communication link 112 may be a wireless connection using Wi-Fi, Bluetooth, LTE or any other suitable form of wireless communication. Computer 104 may collaborate with other computers such as a server 160 coupled to computer 104 by a communication link 162. The link 162 may also be any suitable wired or wireless connection that allow computer 104 and server 160 to determine one or more operational aspects or settings of the imaging system 100.

The imaging device 108 may include an imaging assembly 116, such as a C-arm, for capturing images of a subject 136. Subject 136 may be any suitable target for imaging, examples of which include, but are not limited to, a human or animal, a specimen, a patient in a hospital under the care of a doctor, or any object for which an image of the internal structure may be obtained using the imaging device. Imaging device 108 may be any suitable type and may include one or more emitting or sensing elements. For example, assembly 116 may include an electromagnetic radiation source 117 useful for emitting electromagnetic energy 141 such as x-rays, and an electromagnetic radiation detector 118 useful for detecting electromagnetic energy, preferably energy that has passed through the subject 136. The assembly 116 is attached to a base 122, which may be mobile, and may include a controller 126 mounted within a housing 142. A user interface 143 may be included in the imaging device which is configured to accept input from a user to provided operational settings to the imaging device. These operational settings may be provided to controller 126, to computer 104, to computer 160, or to other aspects of the imaging system to control the imaging process.

A support structure 132, such as a table, may be included to properly position subject 136 between the radiation source and radiation detector so that radiation 141 passing through may be used to generate an image of the internal structures of the subject. In this example, the source 117 is oriented vertically below the subject, and the detector 118 is above the subject. However, this configuration is only exemplary rather than restrictive as the source and detector aspects of the imaging assembly 116 may be arranged in any suitable configuration. For example, the source and detector may be inverted from what is shown with the detector below and the source above the subject, or they may be arranged horizontally with the subject standing, sitting, or otherwise positioned between the emitter and detector, to name a few other possible configurations.

Radiation source 117 may be any suitable type of emitter. In the case of an x-ray emitting radiation source, the source 117 may include an x-ray tube configured to convert electrical input power into x-rays. The x-ray tube may include an evacuated chamber surrounding a heated filament often referred to as the cathode, the filament being positively charged and configured to generate a beam of electrons that strike an anode such as a rotating tungsten disk. The electrons may strike the anode at high-speed due to a very high potential difference between the cathode and the anode. The tungsten material absorbs the electrons and releases some of the energy in the form of x-rays.

Any suitable electromagnetic energy within the electromagnetic spectrum may be used by imaging device 108 to generate images, examples of which include but are not limited to, x-rays or gamma rays. For example, creating an image utilizing higher kVp and low mAs in comparison to low kVp and high mAs reduces radiation absorption by the subject or exposure to scatter to the personnel with similar image quality.

In one example, the imaging device 108 is configured to generate an internal image colloquially referred to as an "x-ray", "x-ray image", or more formally as a "radiograph". Such an internal image of a subject may be useful to assist with any imaging procedure such as medical procedures being performed in different regions of the subject's body. Examples of such procedures include, but are not limited to Computed Tomography (CT), general fluoroscopy, surgical fluoroscopy, interventional fluoroscopy, such as in the case of a catheterization such as vascular and endo-vascular studies and procedures or other surgical procedures, to name a few non-limiting examples. In another example, the subject may be a manufactured article that is being imaged to detect abnormalities or defects using the disclosed system to generate an image of the internal structures of the item.

The internal image may be generated by directing radiation 141, such as X-rays, from the radiation source 117 toward the subject so that a portion of the radiation is absorbed by the body of the subject and a portion of the radiation is captured by the electromagnetic radiation detector 118, such as a fluoroscope or a digital X-ray detector such as a Flat Panel Detector. The imaging device 108 may include an image intensifier 119 that is operable to convert the captured radiation into visible light that has a higher intensity than what may be produced by the source alone. This may allow a viewer to more easily see subtle aspects of the image than might otherwise be invisible. A collimator 120 may also be included for narrowing the field of view thereby operating to reduce or eliminate unwanted x-ray radiation from radiation source 117 that is outside of the region of interest and to direct it more specifically on a particular region. Thus collimator 120 can operate to reduce the overall effective dose to the subject while increasing the likelihood of obtaining a clear image.

Different procedures may require the imaging device 108 to have different operating settings in order to generate a useful image. In the case of x-rays, these operating settings may include the voltage and the tube current exposure time product of the x-ray tube. The voltage may be measured by the kilovoltage peak (kVp), which describes the maximum voltage applied to the x-ray tube and is proportional to the energy of the x-ray photons emitted from the electromagnetic radiation source 117. Adjusting the kilovoltage peak may be used to adjust the contrast of the x-ray image, as different body parts may require a certain minimum kVp setting that will generate x-rays with enough energy to penetrate and pass through the target item or region of the body.

Another possible operational setting that may impact the image produced by imaging device 108 is the tube current exposure time product (mAs). The tube current exposure time is a calculation of the current passing through the x-ray tube creating the x-rays and the time that the tube is operated and may be used to control radiographic density. Larger values of the tube current exposure time product indicate greater radiation and can increase the number of x-ray photons that are absorbed by the body of the subject and that are collected by the radiation detector 118. As an example, a greater tube current exposure time product may be helpful when imaging larger areas of a subject, while a lower tube current exposure time may be sufficient for imaging smaller regions.

Controller 126 of the imaging device 108 may be configured to control these and other operating settings for the imaging assembly 116. In one example, the controller activates an auto exposure mode that, among other aspects, automatically determines desirable operational settings by activating the imaging assembly 116 to generate multiple images in sequence using different combinations of kVp and mAs values for each image until an image of acceptable clarity is produced. However, this repeated exposure to multiple imaging cycles results in additional radiation absorption by the subject, and by the individuals operating the imaging system. If this automated search for a desirable operational setting occurs multiple times in a given session, thus the overall radiation absorption can be far in excess of the actual radiation required to generate one or two useful images thus increasing the overall radiation exposure per useful image.

The disclosed imaging system may use aspects of the medical procedure, information about the subject, information about the particular imaging system being used, and the like, to optionally disable the Automatic Exposure Control and determine suitable or optimal operating settings for the imaging device 108 without the need for repeated radiation exposure.

In one example, the controller 126 may automatically determine which settings are optimal for reducing overall radiation exposure using internal control logic 127 which may be installed in controller 126 as hard-wired logic circuits or preprogrammed Application Specific Integrated Circuits (ASICs), or load into more generic processing circuitry of controller 126 as software, or any suitable combination of these. Inputs into the control logic may be received from a user interface coupled to the controller, or from information obtained about the subject in advance of the procedure and loaded into the controller.

In another aspect, the control logic for controller 126 may be installed as control logic 128 in computer 104, either as application specific circuitry, or as software, or a combination thereof. In this configuration, controller 126 may determine the settings by sending a request for settings to computer 104. In another example, controller 126 may determine the settings by accepting input or commands from computer 104 indicating what the settings will be. Inputs into the control logic 128 may be received from a user interface generated by computer 104, or from information obtained about the subject in advance of the procedure and loaded into the controller. In this way computer 104 may be configured to take over control of the imaging system thus overriding some or all of the controller functions provided by controller 126.

In another aspect, the control logic for controller 126 may be installed in server 160 as control logic 129, either as application specific circuitry, or as software, or a combination thereof. In this configuration, controller 126 may determine the settings by sending a request to server 160 for settings. In another example, controller 126 may determine the settings by accepting input or commands from server 160, received either via computer 104 and communication links 162 and 112, or via a communication link 163 between controller 126 and server 160. In this way, server 160 may use control logic 129 to determine what the settings for imaging system 100 should be. Determining controller settings in this example includes processing and decision making processes optionally provided by the server 160, with or without the help of computer 104. The server may thus be configured to take over control of the imaging system thus overriding some or all of the controller functions provided by controller 126.

Figure 2:
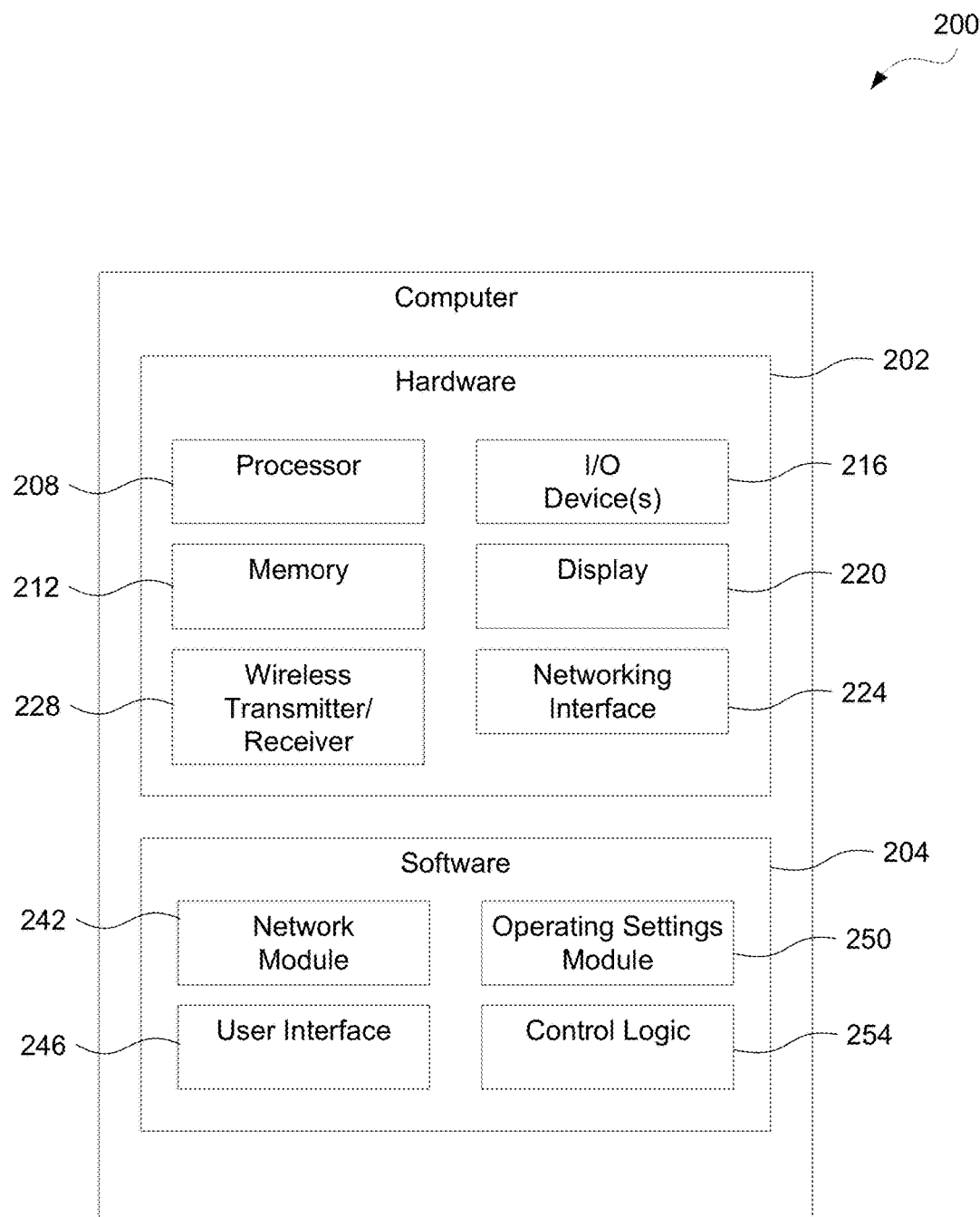
FIG. 2 illustrates a component view of one example of a computer usable with the radiation reduction system of the present disclosure.

FIG. 2 illustrates aspects of a computer that may be useful for controlling the disclosed imaging system. These aspects may be included in server 160, in computer 104, in controller 126, or elsewhere in the system. Aspects of a computer that may be generally grouped together as hardware 202 and software 204. The hardware component 202 of the disclosed computers may include a processor 208 and memory 212. A user, or other collaborating computer, may interact with the computer using a user interface 216 which may include any suitable input or output (I/O) device 216, such as a keyboard, mouse, or touchscreen. A display 220 may be included to present information to the user. A networking interface 224 may be included and configured to connect the computer to a computer network such as a local area network or the internet. A wireless transceiver 228 may also be included to facilitate and manage transmission and receipt of wireless signals, such as in the case where the computer has established a wireless communication link with another computer.

The software components 204 of the disclosed computers may include a network module 242 for controlling networking interface 224 and a user interface module 246 configured to generate a user interface and provide access to that user interface using I/O devices 216. An operating settings module 250 may be used to determine operating settings for imaging device 108, computer 104, server 160, and the like. In some examples, the software component may also include control logic 254 configured to determine control commands to controller 126 of the imaging system. Controller 126 may then accept these commands as input and configure the operational settings of the imaging device 108 as specified by operating settings module 250.

In one example, the computer 104 provides output using the display 220 and the user I/O device 216, and may then accept input accordingly that may be used by operating settings module 250 to determine the operating settings for the imaging device 108. In another example, the server 160 accepts input from a user interface generated by server 160, from computer 104, or from controller 126, and provides output using, for example the display 220, the user I/O device 216, or networking interface 224, to determine the operating settings for the imaging device 108.

Figure 3:
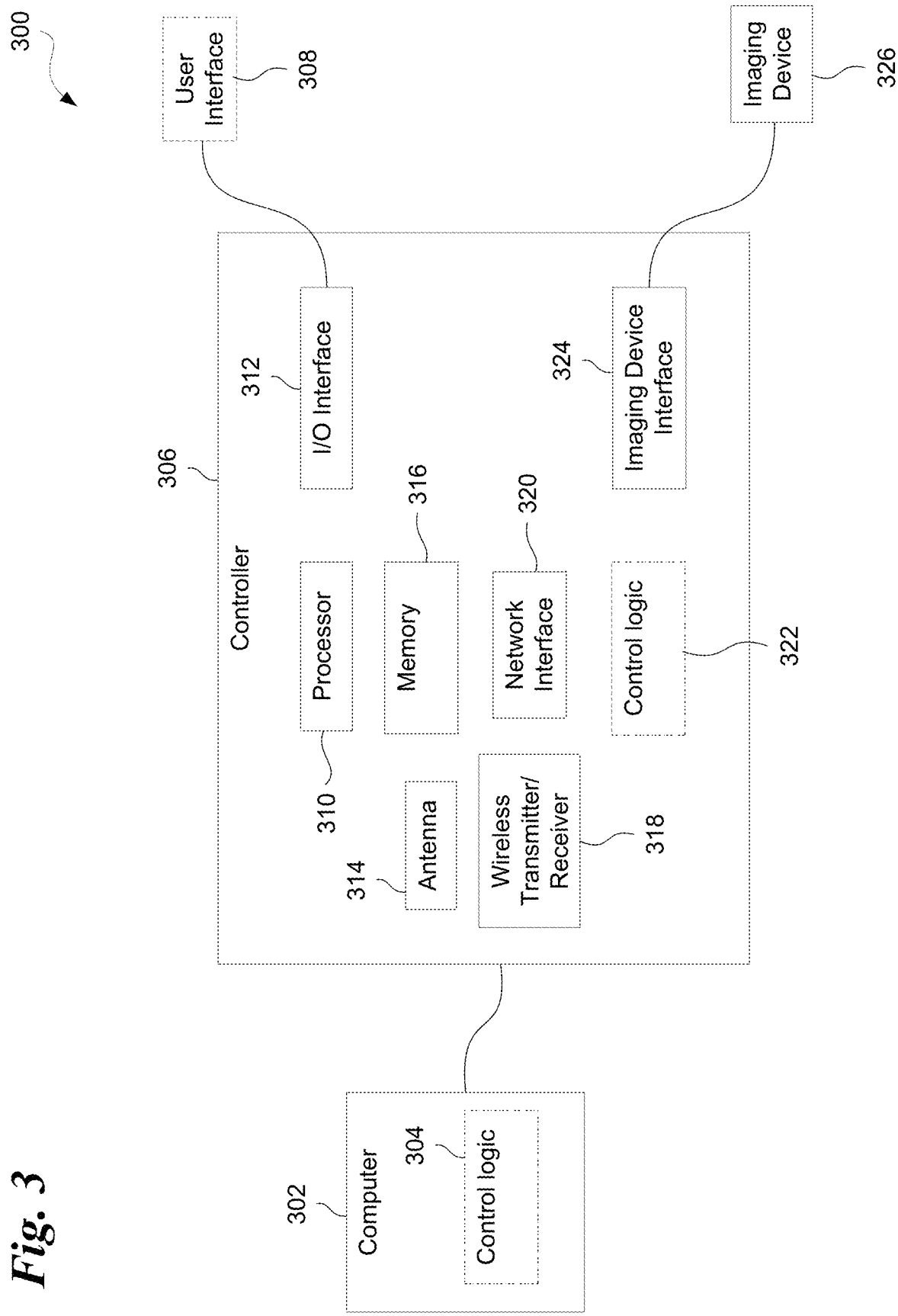
FIG. 3 illustrates one example of components that may be included in a controller of present disclosure.

FIG. 3 illustrates at 300 examples of components that may be included in a controller 126 for the disclosed imaging system, or for other similarly functioning controllers disclosed herein. In this example, a controller 306 includes a processor for performing logical operations, or other computational tasks, and an Input/Output Interface 312 configured to couple controller 306 to an optional user interface 504 for accepting input from a user. Examples of such a user interface are disclosed herein elsewhere. Controller 306 may include an antenna and a wireless transmitter and/or receiver 318 for communicating wirelessly with other computers such as computer 302. Here also is illustrated the concept discussed earlier where control logic for determining the operational aspects of the disclosed system may optionally be included in controller 306 as hardware or software (or both) at 322, or at 502 as either hardware or software (or both) in a remote computer such as computer 302. Operating parameters, commands, or other information may be retained in a memory 316, and a networking interface may be included for managing communication protocols and other related processing to enable controller 306 to communicate with other computers on a computer network. An imaging device interface 324 may be included to manage and control communications between imaging device 326 and controller 306 where imaging device 326 is any type of imaging device according to the present disclosure.

In another aspect, a controller of the present disclosure may be configured to accept input from a user interface of the imaging device (such as user interface 143, 308, or other such interface) and pass that input to the imaging machine, to a computer in communication with the controller, or both. The controller may also be configured to accept input from a computer in communication with the controller, and in turn pass that information to the imaging machine, to the user interface of the imaging machine, or both. In this way, the controller may be useful as a pass through control interface couple the imaging machine to multiple user interfaces so that updates made to settings in one user interface may be reflected some or all of the other user interfaces coupled to the imaging device.

For example, a computer such as a server computer 160 may include control logic 129 configured to change operational settings for the imaging device. This server may be coupled to a controller liked 126 or 306 (or another) that is configured to automatically determine values for the operating parameters of the imaging device, and send them to the controller directly via communication link 163, or indirectly via a computer 104 and communication links 162 and 112. These values may then appear on user interface 143.

In another example, a user may enter values using computer 104, and the control logic 129 may be retained in server 160. The values may be passed to server 160, the control logic engaged, and the resulting values updated on the user interface of computer 104 via communication link 162, and on user interface 143 via communication links 163 (direct to the controller), or communication links 162 and 112 (via an intermediate computer).

In another example, a user may enter values into user interface 143, and those values may be passed directly to server 160 via communication link 163, and/or to computer 104. In this example, the control logic may be 128 in computer 104, 129 in computer 160, or 127 in the controller itself within the imaging device itself. These are but a few non-limiting examples of how the control logic may be positioned in any computer in communication with the controller, or in the controller itself, and updates to the settings of any of these devices may be fed to the control logic in any other connected device so that a determination can be made as to how to reduce the overall radiation dose while obtaining a useable image.

Figure 4:
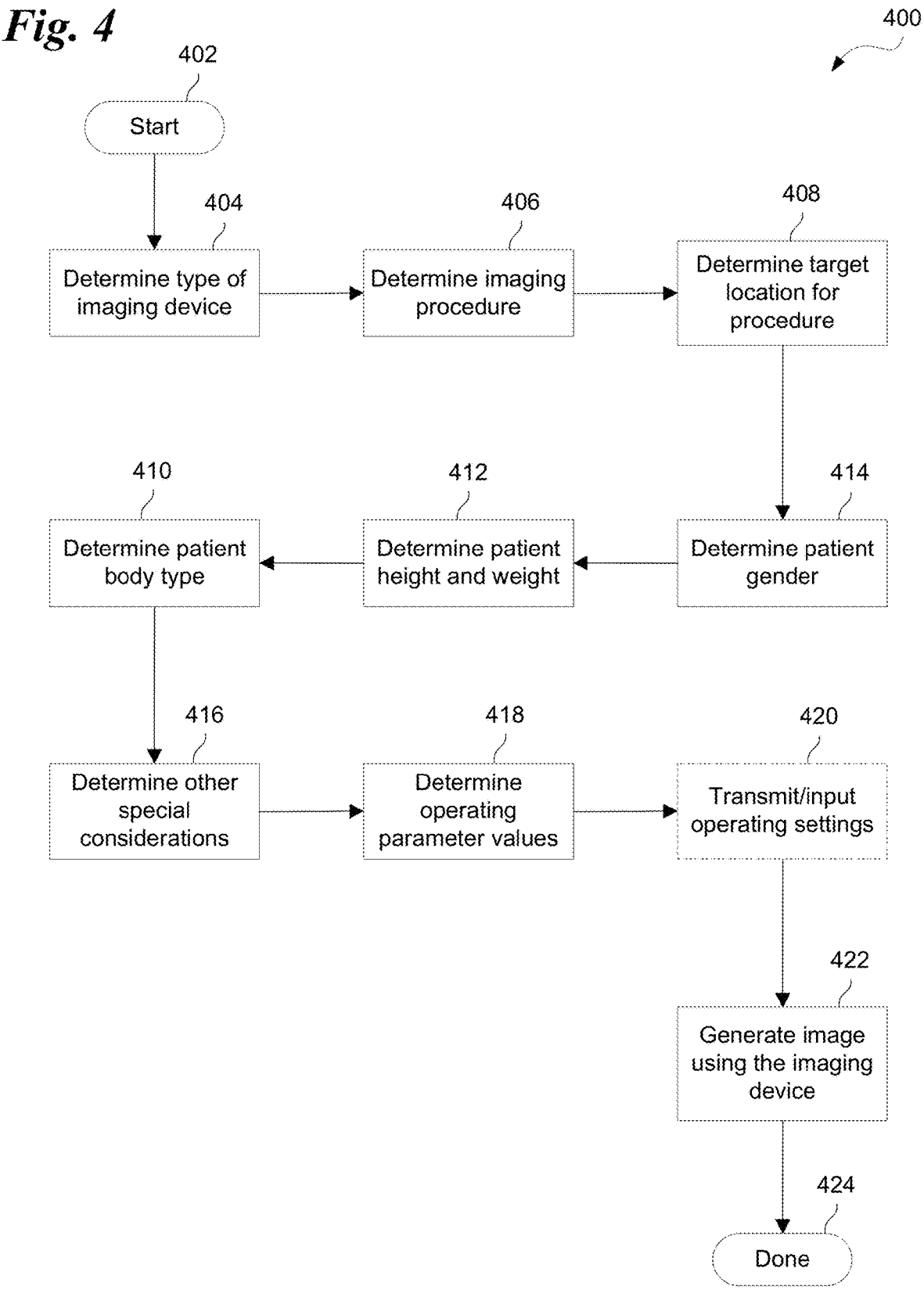
FIG. 4 illustrates a flowchart for a method of operating an imaging system of the present disclosure.

FIG. 4 illustrates some of the operational details that may be performed by the disclosed imaging system to reduce overall radiation exposure. Beginning at 402, the system may determine the type of imaging device involved at 602, such as by accepting input from an operator using a user interface as disclosed herein. In another example, the controller (such as controller 126, 306, and the like) may obtain this information directly from the imaging device without operator input. The type imaging device obtained at 602 may include the brand or manufacturer of the imaging system and may also include further specificity, such as the model of imaging system, the operating parameters that are available for automatic adjustment, threshold limits on these operating parameters, or other special attributes specific to different imaging devices.

The system may be configured to determine the type of imaging procedure to perform at 406. This again may be obtained by accepting input from a user via a computer coupled to the controller, or from the controller itself. Examples of procedures that may be performed include, but are not limited to medical procedures for interventional pain, general surgery, cardiology, orthopedics, fluoroscopy, or neurosurgery. In other embodiments, other desired imaging applications may also be included. For example, one of these, or other options may be selected by a user, which is to say the procedure may be picking as an option from a list that is already populated with a closed set of options, or it may include other input such as a user entering an option that is not provided in a prefilled list.

In another aspect, the target location for the procedure is determined at 408. As in previous examples, this may be entered as input obtained by a user interface, or by any other suitable means. For example, an operator might select a knee from a diagram of the human body that is presented on a display device by a computer or a controller of the imaging system in the case where a knee is the area of the subject's body that is to be imaged.

In another aspect, the system may determine physical characteristics of the subject. These may include gender at 414, height and weight at 412, and patient body type, or any combination thereof. These may be obtained as input from a user via a user interface, or by other suitable means such as, in the case of weight for example, via a scales configured to feed weight information directly to the controller or a collaborating computer.

In another examples, the user interface may be configured to accept input defining a subject body type that includes choosing from a list of body types, or the input may be accepted as a selection from different general shapes that generally indicate those areas where the subject's weight is concentrated. For example, a collection of one or more representative depictions recognizable as human shapes or outlines may be provided to aid in selecting a body type. The system may also determine other special considerations at 416 that may need to be accounted for during the imaging process. For example, if the subject has a metal implant or if the subject has some other type of prosthesis near the imaging site as discussed herein.

The determinations made by the system may be used to determine which operating settings of the imaging system to adjust, and to what degree at 418. This determination may be made by any of the disclosed computers or servers, or by any of the disclosed controllers, either separately, or by collaborating together. For example, a computer communicating with the imaging system controller as illustrated in FIG. 1 may accept input from the imaging system, and/or from the user via a user interface and may use installed control logic to determine which settings to adjust and what the parameter values should be.

In another example, the controller may obtain input from a user, and pass that input to a remote server which may be configured to determine the settings to change and what the new values for the imaging system should be. These settings may then be communicated back to the controller. In another example, the controller may calculate the resulting parameter values using the disclosed control logic. This calculation may be based on other input from a user received as needed via a user interface of the imaging device itself.

In another example, the system may determine the operational parameters and provide them to an operator via a user interface of the system where the operator may visually observe the generated operating settings and may manually adjust them if desirable to fine tune the image quality. This user interface may be provided by any of the disclosed computers, or by the controller itself.

The operational parameter values may be provided to the imaging device 108 at 420 and the imaging process may be initiated to generate an image at 422 using the calculated operating settings to reduce the overall radiation applied to the subject while obtaining a medically useful image or set of images.

Figure 5:
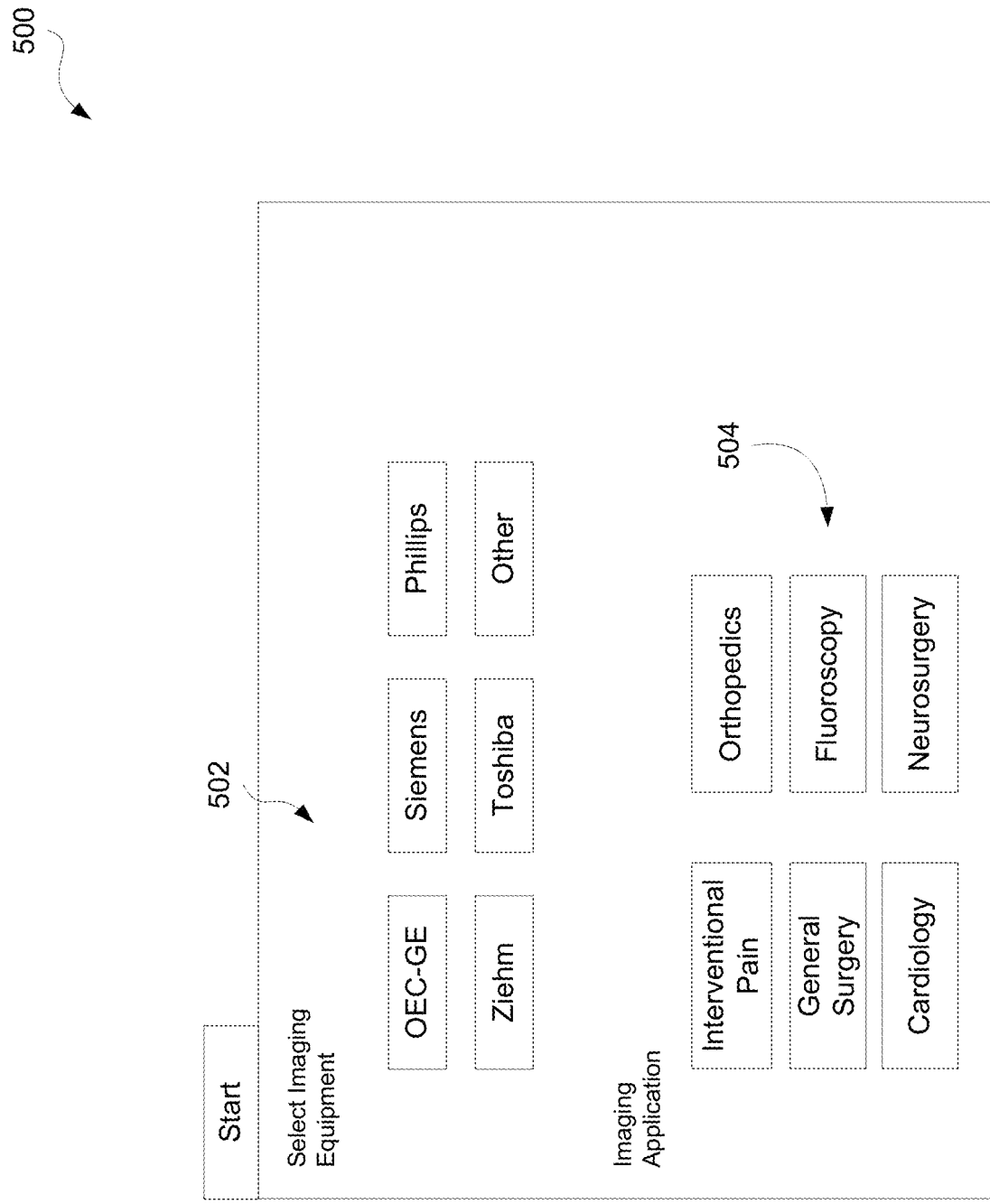
FIG. 5. illustrates one example of a user interface for operating the disclosed imaging system.

FIGS. 5-9 illustrate examples of a user interface that may be provided by the disclosed system to accept user input in determining aspects of the subject and the procedure which may be useful in obtaining a useful image with minimum radiation exposure. In FIG. 5 at 500 is illustrated a start screen that may be displayed to a user such as a qualified medical professional or other operator. The start screen 500 may include a list 502 of different manufacturers or brands and/or models of imaging equipment that may be used during an imaging procedure. In this example, the list 502 may include other sublists, such as in a hierarchical arrangement starting first at the highest level with manufacturers or brands. When a user provides input selecting a manufacturer or brand, the system may accept this input and may be configured to generate and provide for display a sublist of models associated with the selected brand or manufacturer. Such selection and query behavior may be provided, for example, by a user interface module 246 of one of the disclosed computers, or by the controller of the imaging device. In another example, the list 502 may include separate entries in the same list showing all supported brands and models in a single list. In another example, a computer (like computer 104) coupled to a an imaging system controller (like controller 126) may automatically send a predetermined request to the controller requesting information about the brand and model of the imaging machine, and may prepopulate the start screen with information from the response thus simplifying the selection process by preselecting or prefilling the list 502 with the best match that the system could find based on this input from the imaging device and/or the controller.

The start screen 500 may also include a list 504 of medical applications for the disclosed imaging process. Different imaging procedures may require different types of imaging techniques and operating settings to reduce the overall dose of radiation, and therefore selecting the particular type of procedure for which the imaging equipment is to be used provides input from which to determine relevant operating settings useful for generating an image suitable for the selected imaging applications. This list may, for example, include different medical procedures that often require some type of imaging. These procedures may be grouped generally to include interventional pain, general surgery, cardiology, orthopedics, fluoroscopy, or neurosurgery. Other examples of start screen 500 may include different applications other than medical procedures, or other applications in general as new applications may be found for the disclosed system and method.

Figure 6:
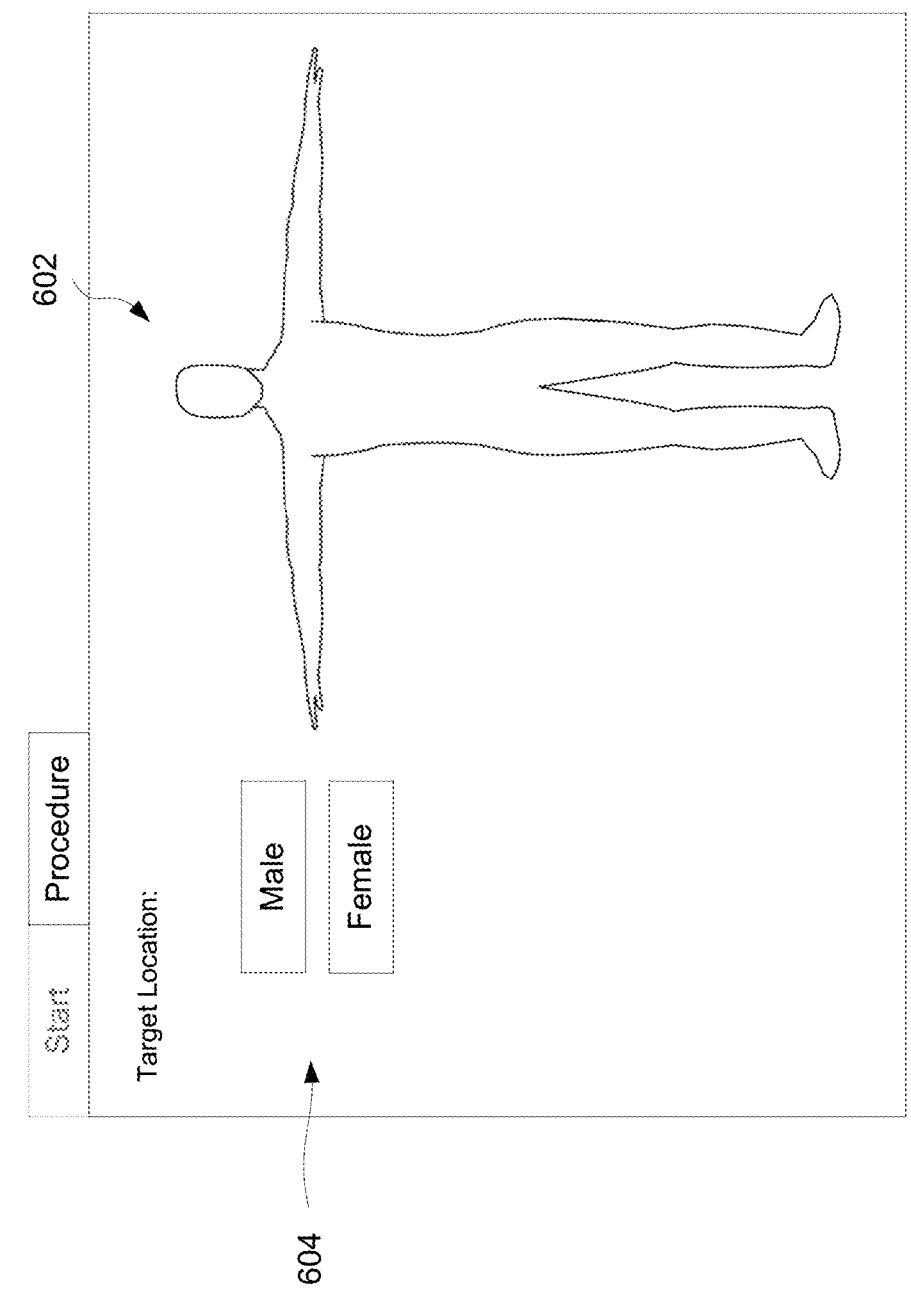
FIG. 6 illustrates another example of a user interface for operating the disclosed imaging system.

In another aspect, a procedure screen may be included in the user interface, on example of which is illustrated in FIG. 6 at 600. The procedure screen may allow a user to specify the specific area or anatomy of the subject that is to be targeted during the imaging procedure. For example, different locations of the body may have different characteristics for absorbing radiation due to differences in bone density and muscle mass in varying body parts. Selecting the specific portion of the body that is to be imaged provides is one way the system may obtain input that can be used to determine the correct operating settings so that they can be automatically applied.

As illustrated in FIG. 6, the procedure screen 600 may include a diagram 602 of a human body and the user may select a portion of the subject's anatomy that is to be imaged by selecting the desired location using the diagram 602. In another example, the procedure screen 600 may provide a list of different portions of the anatomy and the user may select the desired body part or portion of the subject's anatomy from the list. The procedure screen 600 may also include a gender selection aspect 604 configured to allow a user to choose whether the subject is a male or female. This aspect may be used as well by the system to automatically determine and/or calibrate the settings of the imaging machine to account for variations in male and female anatomy that can affect the quality of the image.

Figure 7:
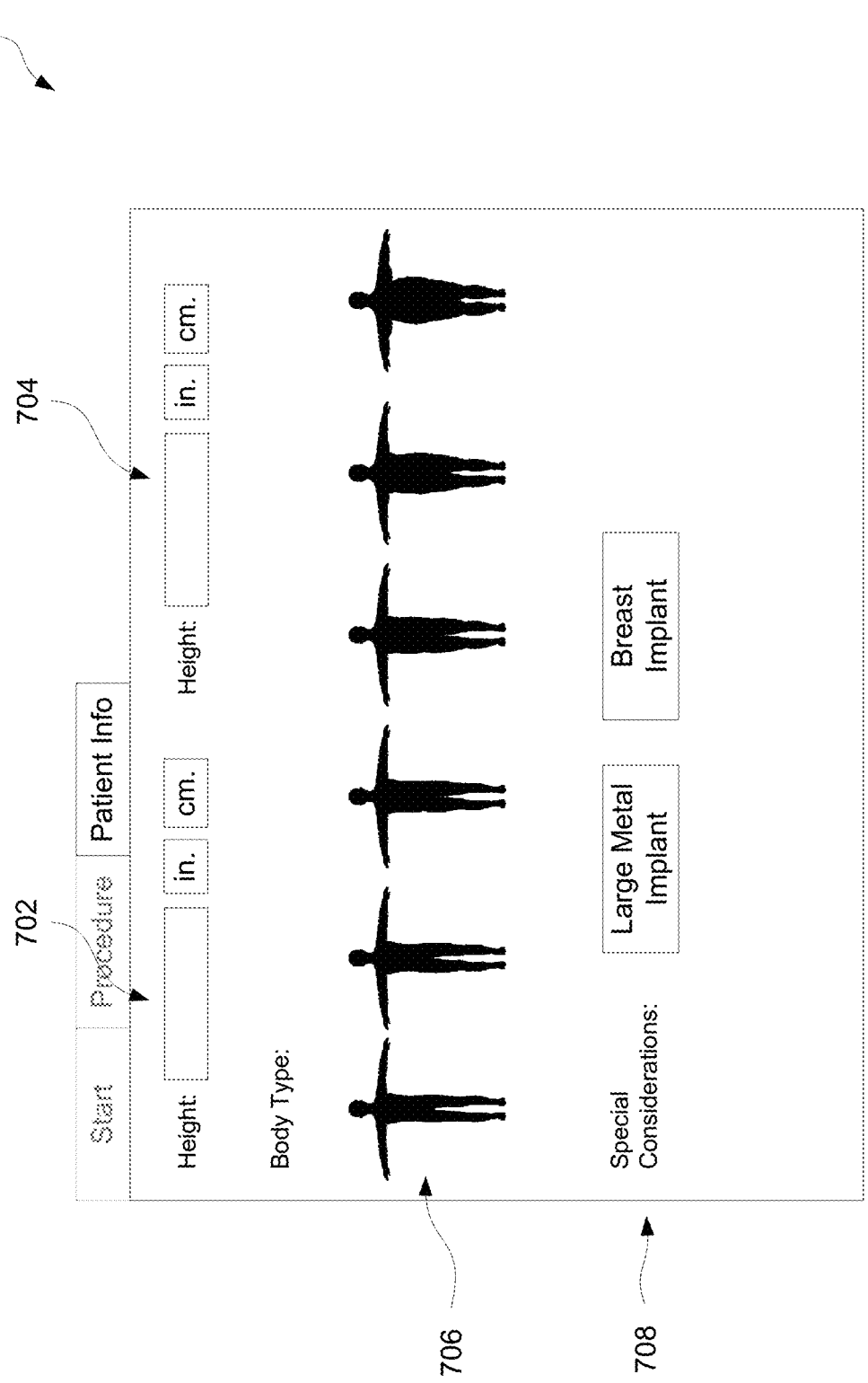
FIG. 7 illustrates another example of a user interface for operating the disclosed imaging system.

In another aspect shown in FIG. 7, the system may provide a subject information screen 700 with a user interface accepting input defining the patient's body type, and other considerations of interest. For example, the information about the subject may be obtained via input captured by user interface controls arranged and configured to accept input defining the subject's height at 702 and a weight at 704. The height input 702 and/or the weight input 702 controls may be configured to allow a user to input the height and weight in either English units (i.e., inches and pounds) or in metric units (i.e., centimeters and kilograms). In another aspect, the height and weight inputs may be directly entered by a user using an input device such as a keyboard, or in some embodiments, a list of heights and/or weights may be displayed and the user may select the desired values from the list that most closely match the subject.

The subject information screen provided at 700 may also include user interface controls for accepting input defining a body type selection 706. The body type or "body habitus" selection 706 may present a collection of shapes representative of different body types that correspond to different build, physique, or general bearing or bodily proportions. These may be useful in adjusting the radiation output as needed for the given procedure to obtain a medically useful image. For example, the body type selection list may include one or more images or icons representing different aspects of bodily proportions for a human or animal subject thus providing input informing the system of the subject's overall anatomical features. The user may select the shape that best matches the overall shape of the subject, or best matches the relevant anatomical features of the individual or the of the target area to be imaged. This input may be used by the system to adjust operational settings of the imaging device based on how a subject's weight is distributed. For example, a subject with a larger lower body may require more powerful radiation for imaging their abdomen than for imaging their upper body. Other useful inputs may be included in the user interface such as controls defining a measurement for arm span, skinfold thickness, mid-upper arm circumference, and the like.

A special considerations selection 708 on the subject information screen 700 may be configured to accept input defining other factors that may be considered when determining operating settings for an imaging device. Examples include implants, artificial limbs, pins, screws, artificial joints, and other foreign materials that may be found in a subject's body. These foreign materials may cause scattering or other interference in the absorption of electromagnetic radiation directed at the body and may thus have a negative effect on the quality of the image if they are not accounted for. In another aspect, the special considerations selection 708 may display all possible special considerations directly on the subject information page 700. In another aspect, the special considerations selection may be configured to accept input which when received is processed by the system to generate an additional drop down list of detailed aspects related to the initial selection that taken together provide additional input for further refining the imaging machine settings.

Figure 8:
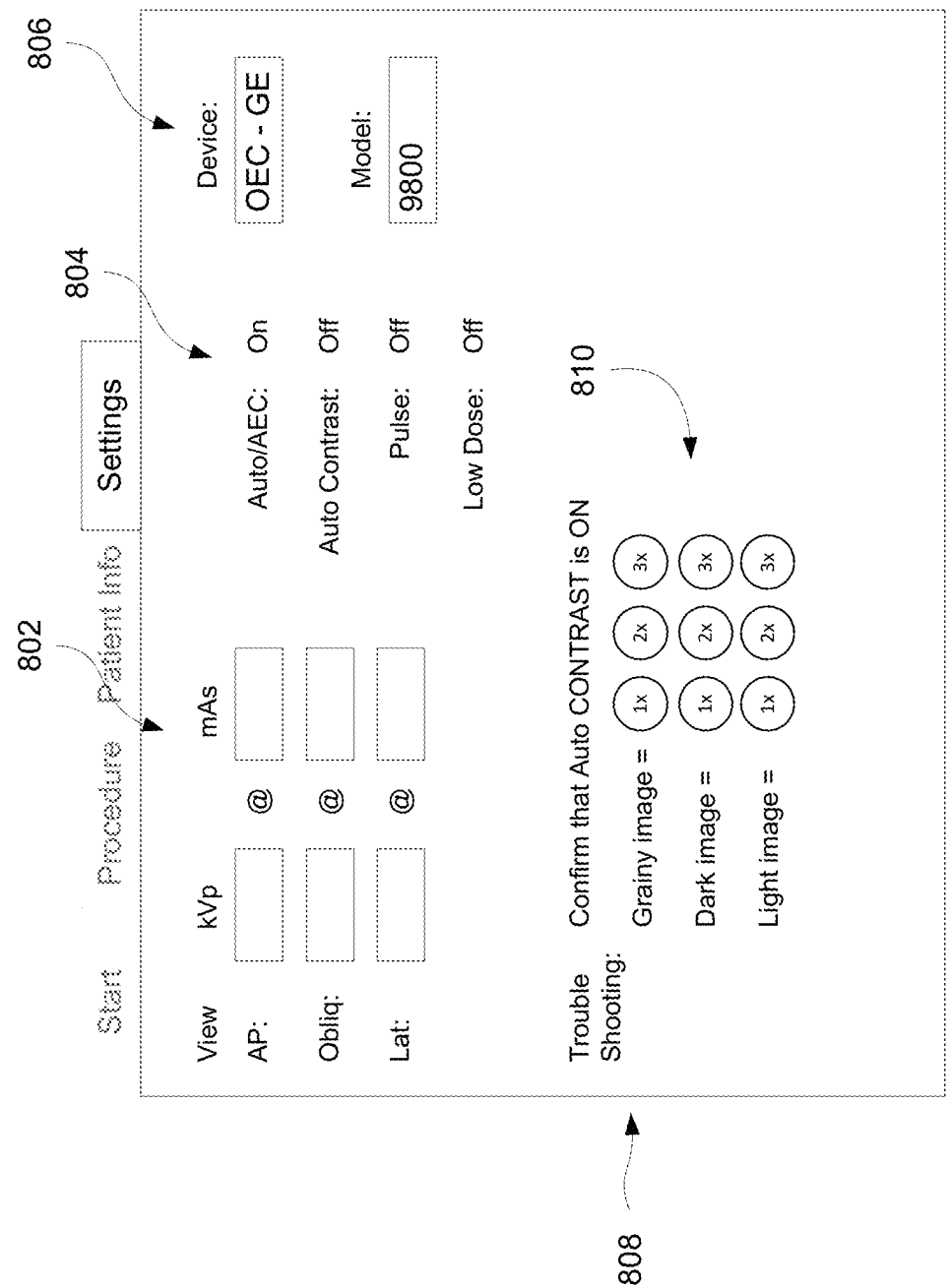
FIG. 8 illustrates another example of a user interface for operating the disclosed imaging system.
Figure 9:
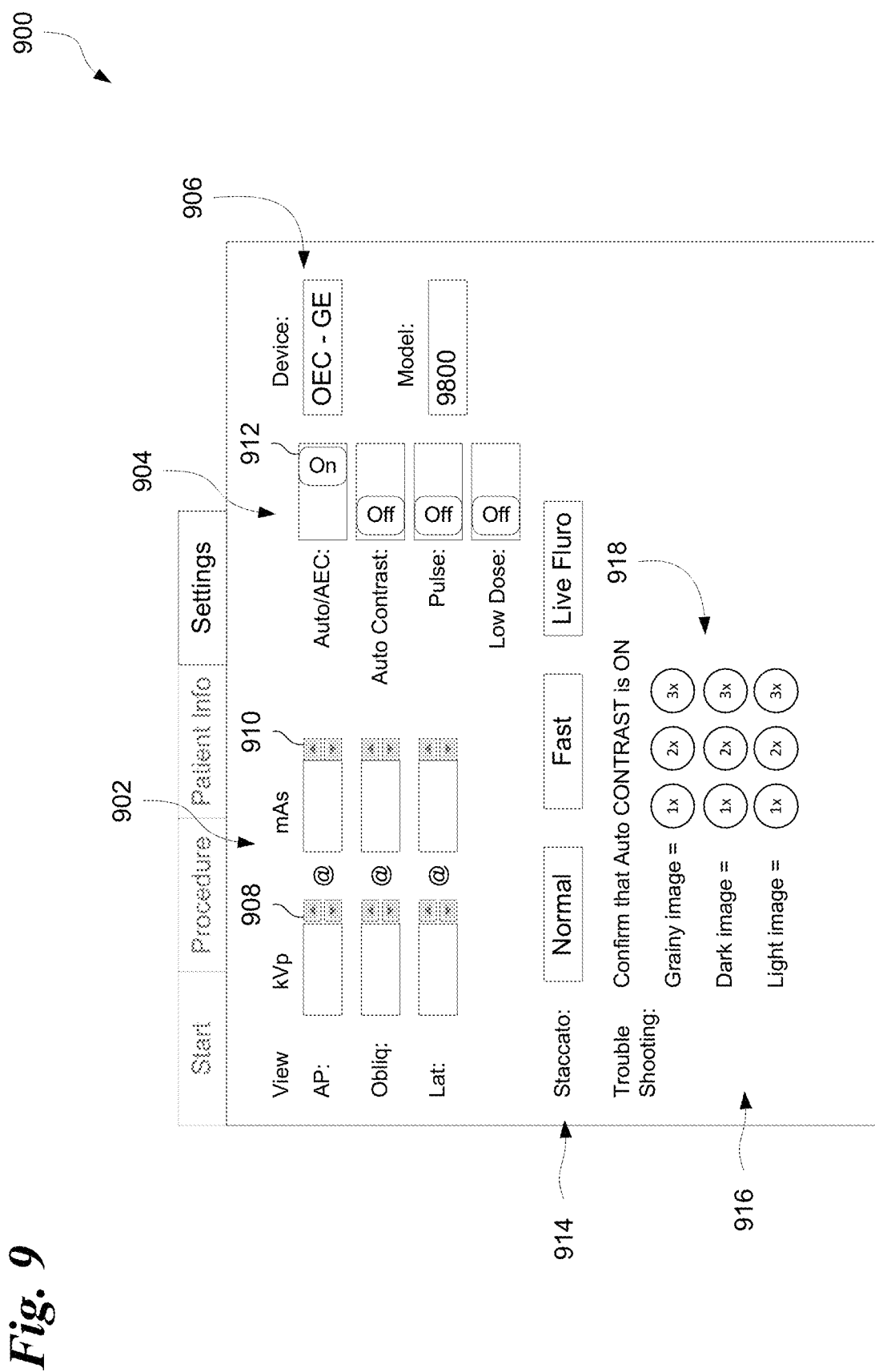
FIG. 9 illustrates another example of a user interface for operating the disclosed imaging system.

In another aspect, the user interface module is configured to provide a settings screen, examples of which appear at 800 in FIG. 8, and at 900 in FIG. 9. The settings screen 800 displays the suggested operating settings as determined by the system disclosed herein. These resulting settings are based on the input provided by the user in the start screen 500, procedure screen 600, and subject information page 700 as outlined above. The settings screen also provides confirmation of the user's input such as with an imaging device indicator 806 that displays the brand and/or the model of the imaging device that was selected by the user at the start screen 500.

The settings screen 800 also includes a radiation values section 802 that optionally displays the values for the operating settings that were determined by the system, such as by using the operating settings module 250. The radiation values section 802 may include different values depending on which views are used for imaging. For example, these views may include anterior/posterior, oblique, and lateral views. The radiation values section 802 may provide operational values for the kVp and the mAs for each of the views that are based on the inputs provided by the user.

A controller settings section 804 may also be provided on the settings screen 800 that is configured to display the controller options specific to a given model of imaging machine that are set to be activated or deactivated based on the user input provided. In the example shown in FIG. 8, the controller settings include auto exposure or "Auto/AEC", auto contrast, pulse, and low dose. Different settings may be shown and adjustable depending on the model and brand of imaging device used. FIG. 8 thus illustrates an example of a user interface display where the system provides feedback as to the current settings the imaging process either will use, or has used depending on whether the image is about to be taken, or already has been taken.

A troubleshooting section 808 may also be provided on the settings screen 800 to offer guidance with techniques or methods to improve image quality if the calculated settings shown in the radiation values section 802 do not produce an optimal image. These techniques may include methods for improving grainy images or images that are either too light or too dark by selecting the correct adjustments. The system may then adjust the relevant setting by a predetermined increment, or by twice the predetermined increment, or by three times the predetermined increment, or more, as illustrated by the selection buttons or icons at 810.

In another aspect, the user interface module may be configured to display an interactive user interface control in troubleshooting section 808 which may be configured to accept input from a user defining additional details about which settings seemed to work best for a given scenario, or what adjustments seemed most helpful or most useful. These user defined troubleshooting aspects may be stored by the system such as in a memory of a computer like computer 104 or 160, or in a memory of a controller like controller 306. In another aspect, these trouble shooting aspects may be related to a specific combination of settings or input provided by the user so that if the same or similar settings come up again later, the specific relevant user defined troubleshooting information may be displayed automatically.

In another aspect, the system may provide a settings screen like the one shown at 900 in FIG. 9. In this example, the user interface module optionally provides controls configured to accept input from the user suitable for adjusting some or all of the settings that a user might otherwise change manually. In this example, a user may manually adjust operating settings of the imaging device during operation thus overriding some or all of the operational settings determined by the disclosed system. As shown in FIG. 9, the settings screen 900 may have a similar layout to the settings screen 800 shown in FIG. 8, including an imaging device indicator 906, a radiation values section 902, a controller settings section 912, and a trouble shooting section 916, or any combination thereof.

The image device indicator 906 may display the brand and the model of the imaging system in use. The radiation values section 902 displays the kVp and the mAs values that are used as the operating settings for the imaging device. Controls 908 and 910 are positioned next to each kVp and mAs value respectively. Controls 908 ad 910 may be used to directly adjust the corresponding operating setting of the imaging device. In the example shown in FIG. 9, the controls 908, 910 include an up arrow and a down arrow. A user may click or push the up arrow to increase the kVp or the mAs by a predetermined interval or the user may click or push the down arrow to decrease the kVp or the mAs by a predetermined interval. In some embodiments, the user may input a specific kVp or mAs value into the radiation values section 902 using an input device such as a keyboard rather than using the controls 908, 910 to adjust the kVp or mAs value. The controller settings section 904 displays different controller options such as Auto/AEC, auto contrast, pulse, and low dose and whether these options are turned on or off. A user may turn these options on or off by selecting the sliders 912 next to the desire option. Any suitable types of user interface controls may be used to select or input the imaging device settings.

The disclosed system may also provide a Staccato setting option as an alternative to live fluoroscopy. Screen 900 optionally provides inputs controlling Staccato setting at 914. The Staccato setting can reduce radiation exposure by utilizing manual, or in this case, automatic computer controlled, pulse imaging. Any of the disclosed computers such as computer 104 or 160 may be used to automatically control the imaging system to operate in this way. In this example, a user may choose to use either a normal or a fast staccato setting. These options may each be displayed as user interface controls on a screen of a computer as disclosed herein, or optionally displayed on a screen of the controller. Additional Staccato speeds may be included such as a slow staccato setting, or the staccato setting may be displayed as a range of numbers and the user interface controls may be configured to accept input defining the speed, or range of speeds, to be used. These speeds may be specified in any suitable format such as by a number of images the system is to take per second.

Additional combinations of features that may be included in the disclosed system are included in the following numbered examples:

1. A system that includes an imaging device configured to capture an image of a subject using electromagnetic radiation, the imaging device defining operating settings for controlling the behavior of the imaging device; and control logic configured to automatically determine the operating settings using criteria that includes a specific type of imaging procedure to be performed, a target location of the subject and at least one physical characteristic of the subject, or any combination thereof, and wherein the operating settings automatically determined by the computer include peak kilovoltage, tube current, exposure time, or any combination thereof;

wherein the operating settings are transmitted from the control logic to the imaging device, and the imaging device is responsive to the control logic and is configured to apply the operating settings to generate an image of the subject using the calculated operating settings.

2. The system of any preceding example, including a computer remote from the imaging device, and a communication link between the imaging device and the computer, wherein the control logic is in the computer, and wherein the operating settings are transmitted from the computer to the imaging device using a communication link electrically connecting the computer to the imaging device.

3. The system of any preceding example, wherein the computer has a user interface that is configured to accept input defining the operating settings, and wherein the input includes information identifying the imaging device, the specific type of imaging procedure to be performed by the imaging device, the target location of the subject which is to be imaged by the imaging device, and the physical characteristics of the subject that include subject gender, subject body type, and subject weight.

4. The system of any preceding example, wherein the communication link includes a wire electrically connecting the computer to the imaging device.

5. The system of any preceding example, wherein the communication link includes a wireless connection electrically connecting the computer to the imaging device.

6. The system of any preceding example, including a first and a second computer, both remote from the imaging device; and a first communication link between the imaging device and the first computer; and a second communication link between the first computer and the second computer, wherein the control logic is in the second computer, and wherein the operating settings are transmitted from the second computer to the first computer using the second communication link, and wherein the operating settings are transmitted from the first computer to the imaging device using the first communication link.

7. The system of any preceding example, including a controller configured to activate and deactivate the imaging device, wherein the control logic is in the controller, wherein the controller is mounted in a housing of the imaging device and is configured to control the imaging device to generate an image of the subject using the calculated operating settings.

8. The system of any preceding example, including a computer remote from the imaging device; and a communication link between the controller and the computer, wherein the operating settings are transmitted from the computer to the controller using a communication link electrically connecting the computer to the controller.

9. The system of any preceding example, including an imaging system user interface of the imaging device that is arranged and configured to accept input defining the operating settings, or any combination thereof wherein the controller is arranged and configured to automatically accept input from the imaging system user interface and send it to the computer; and wherein the controller is arranged and configured to automatically accept input from the computer and adjust the user interface and the operating settings of the imaging device accordingly.

10. The system of any preceding example, including a computer remote from the imaging device;

a controller configured to activate and deactivate the imaging device; and a communication link between the controller and the computer;

wherein the control logic is in the computer and the controller is responsive to accept operating settings from the computer; and wherein the controller is mounted in a housing of the imaging device and is configured to control the imaging device to generate an image of the subject using the operating settings.

11. The system of any preceding example, including an imaging system user interface of the imaging device configured to accept input defining the operating settings, wherein the controller is responsive to the imaging system user interface, and wherein the controller is configured to send the operating settings received from the imaging system user interface to the computer using the communications link.

12. The system of any preceding example, including a computer user interface of the remote computer configured to accept input defining the operating settings, wherein the computer is configured to send the operating settings from the computer user interface to the controller using the communications link.

13. The system of any preceding example, wherein the operating settings include information identifying the specific imaging device.

14. The system of any preceding example, wherein the at least one physical characteristic of the subject includes any of subject gender, subject body type, and subject weight, or any combination thereof.

15. The system of any preceding example, wherein the imaging device is configured to perform an automatic exposure control procedure, and wherein the control logic is arranged and configured to control the imaging device to deactivate the automatic exposure control before capturing an image of the subject.

16. The system of any preceding example, wherein the imaging device generates the image by generating x-ray radiation, wherein the x-ray radiation is generated for a period of time about equal to the exposure time, and where the exposure time is less than 1 second.

17. The system of any preceding example, wherein an exposure time required to generate an image is less than about 1 second.

18. The system of any preceding example, wherein an exposure time required to generate an image is less than about 0.6 seconds.

19. The system of any preceding example, wherein a Scatter Rate of the imaging device when activated is less than about 300 mR/hour within 4 feet of the x-ray imaging device.

20. The system of any preceding example, wherein a Scatter Rate of the imaging device when activated is less than about 150 mR/hour within 4 feet of the x-ray imaging device.

GLOSSARY OF DEFINITIONS AND ALTERNATIVES

While examples of the inventions are illustrated in the drawings and described herein, this disclosure is to be considered as illustrative and not restrictive in character. The present disclosure is exemplary in nature and all changes, equivalents, and modifications that come within the spirit of the invention are included. The detailed description is included herein to discuss aspects of the examples illustrated in the drawings for the purpose of promoting an understanding of the principles of the inventions. No limitation of the scope of the inventions is thereby intended. Any alterations and further modifications in the described examples, and any further applications of the principles described herein are contemplated as would normally occur to one skilled in the art to which the inventions relate. Some examples are disclosed in detail, however some features that may not be relevant may have been left out for the sake of clarity.

Where there are references to publications, patents, and patent applications cited herein, they are understood to be incorporated by reference as if each individual publication, patent, or patent application were specifically and individually indicated to be incorporated by reference and set forth in its entirety herein.

Singular forms "a", "an", "the", and the like include plural referents unless expressly discussed otherwise. As an illustration, references to "a device" or "the device" include one or more of such devices and equivalents thereof.

Directional terms, such as "up", "down", "top" "bottom", "fore", "aft", "lateral", "longitudinal", "radial", "circumferential", etc., are used herein solely for the convenience of the reader in order to aid in the reader's understanding of the illustrated examples. The use of these directional terms does not in any manner limit the described, illustrated, and/or claimed features to a specific direction and/or orientation.

Multiple related items illustrated in the drawings with the same part number which are differentiated by a letter for separate individual instances, may be referred to generally by a distinguishable portion of the full name, and/or by the number alone. For example, if multiple "laterally extending elements" 90A, 90B, 90C, and 90D are illustrated in the drawings, the disclosure may refer to these as "laterally extending elements 90A-90D," or as "laterally extending elements 90," or by a distinguishable portion of the full name such as "elements 90".

The language used in the disclosure are presumed to have only their plain and ordinary meaning, except as explicitly defined below. The words used in the definitions included herein are to only have their plain and ordinary meaning. Such plain and ordinary meaning is inclusive of all consistent dictionary definitions from the most recently published Webster's and Random House dictionaries. As used herein, the following definitions apply to the following terms or to common variations thereof (e.g., singular/plural forms, past/present tenses, etc.):

"About" with reference to numerical values generally refers to plus or minus 10% of the stated value. For example, if the stated value is 4.375, then use of the term "about 4.375" generally means a range between 3.9375 and 4.8125.

"Activate" generally is synonymous with "providing power to", or refers to "enabling a specific function" of a circuit or electronic device that already has power.

"And/or" is inclusive here, meaning "and" as well as "or". For example, "P and/or Q" encompasses, P, Q, and P with Q; and, such "P and/or Q" may include other elements as well.

"Antenna" or "Antenna System" generally refers to an electrical device, or series of devices, in any suitable configuration, that converts electric power into electromagnetic radiation. Such radiation may be either vertically, horizontally, or circularly polarized at any frequency along the electromagnetic spectrum. Antennas transmitting with circular polarity may have either right-handed or left-handed polarization.

In the case of radio waves, an antenna may transmit at frequencies ranging along electromagnetic spectrum from extremely low frequency (ELF) to extremely high frequency (EHF). An antenna or antenna system designed to transmit radio waves may comprise an arrangement of metallic conductors (elements), electrically connected (often through a transmission line) to a receiver or transmitter. An oscillating current of electrons forced through the antenna by a transmitter can create an oscillating magnetic field around the antenna elements, while the charge of the electrons also creates an oscillating electric field along the elements. These time-varying fields radiate away from the antenna into space as a moving transverse electromagnetic field wave. Conversely, during reception, the oscillating electric and magnetic fields of an incoming electromagnetic wave exert force on the electrons in the antenna elements, causing them to move back and forth, creating oscillating currents in the antenna. These currents can then be detected by receivers and processed to retrieve digital or analog signals or data.

Antennas can be designed to transmit and receive radio waves substantially equally in all horizontal directions (omnidirectional antennas), or preferentially in a particular direction (directional or high gain antennas). In the latter case, an antenna may also include additional elements or surfaces which may or may not have any physical electrical connection to the transmitter or receiver. For example, parasitic elements, parabolic reflectors or horns, and other such non-energized elements serve to direct the radio waves into a beam or other desired radiation pattern. Thus antennas may be configured to exhibit increased or decreased directionality or "gain" by the placement of these various surfaces or elements. High gain antennas can be configured to direct a substantially large portion of the radiated electromagnetic energy in a given direction that may be vertical horizontal or any combination thereof.

Antennas may also be configured to radiate electromagnetic energy within a specific range of vertical angles (i.e. "takeoff angles) relative to the earth in order to focus electromagnetic energy toward an upper layer of the atmosphere such as the ionosphere. By directing electromagnetic energy toward the upper atmosphere at a specific angle, specific skip distances may be achieved at particular times of day by transmitting electromagnetic energy at particular frequencies.

Other examples of antennas include emitters and sensors that convert electrical energy into pulses of electromagnetic energy in the visible or invisible light portion of the electromagnetic spectrum. Examples include light emitting diodes, lasers, and the like that are configured to generate electromagnetic energy at frequencies ranging along the electromagnetic spectrum from far infrared to extreme ultraviolet.

"Arm Span" generally refers to the distance between the tips of the middle fingers with the arms fully extended. In adults the arm span should equal the height.

"Bluetooth Protocol" or "Bluetooth" generally refers to a wireless technology standard used for exchanging data between fixed and mobile devices over short distances using short-wavelength UHF radio waves in the industrial, scientific and medical radio bands, from 2.402 GHz to 2.480 GHz, and building personal area networks (PANs). It was originally conceived as a wireless alternative to RS-232 data cables.

Bluetooth is a standard wire-replacement communications protocol primarily designed for low power consumption, with a short range based on low-cost transceiver microchips in each device. Because the devices use a radio (broadcast) communications system, they do not have to be in visual line of sight of each other; however, a quasi-optical wireless path must be viable.

Range is power-class-dependent, but effective ranges vary in practice Officially Class 3 radios have a range of up to 1 meter (3 ft), Class 2, most commonly found in mobile devices, 10 meters (33 ft), and Class 1, primarily for industrial use cases, 100 meters (300 ft). Bluetooth Marketing qualifies that Class 1 range is in most cases 20-30 meters (66-98 ft), and Class 2 range 5-10 meters (16-33 ft). The actual range achieved by a given link will depend on the qualities of the devices at both ends of the link, as well as the air conditions in between, and other factors.

The effective range varies depending on propagation conditions, material coverage, production sample variations, antenna configurations and battery conditions. Most Bluetooth applications are for indoor conditions, where attenuation of walls and signal fading due to signal reflections make the range far lower than specified line-of-sight ranges of the Bluetooth products.

Most Bluetooth applications are battery-powered Class 2 devices, with little difference in range whether the other end of the link is a Class 1 or Class 2 device as the lower-powered device tends to set the range limit. In some cases, the effective range of the data link can be extended when a Class 2 device is connecting to a Class 1 transceiver with both higher sensitivity and transmission power than a typical Class 2 device. Mostly, however, the Class 1 devices have a similar sensitivity to Class 2 devices. Connecting two Class 1 devices with both high sensitivity and high power can allow ranges far in excess of the typical 100 m, depending on the throughput required by the application. Some such devices allow open field ranges of up to 1 km and beyond between two similar devices without exceeding legal emission limits.

The Bluetooth Core Specification mandates a range of not less than 10 meters (33 ft), but there is no upper limit on actual range. Manufacturers' implementations can be tuned to provide the range needed for each case.

"Body Height" generally refers to the length from the plantar surface of the foot to the crown of the head.

"Body Size" or "Body Habitus" generally refers to the physical characteristics of an individual and include such considerations as physique, general bearing, and body build. Examples include the more outdated "somatotypes" (mesomorphic—muscular and athletic; endomorphic—rounded and stout; and ectomorphic—tall and thin), which in the past have been correlated with propensity to disease (e.g., habitus apoplectus).

In another more common example, body size and habitus may be used to encompass the more quantifiable measurements of height, weight, body proportions, skinfold thickness, and mid-upper arm circumference. These measurements are not typically associated with "normal" or "abnormal" values, but are generally interpreted in the context of an individual's age, sex, clinical status, and previous measurements. The values can be plotted as a percentile of a reference population or as a percentage of an "ideal" value.

"Body Proportion" generally refers to the trunk to limb ratio and the arm span.

"Body Weight" generally refers to the total weight of the body. Weights greater than 120% of "ideal" suggest obesity, while weights less than 70% of "ideal" may indicate severe malnutrition.

"C-arm" generally refers to a radiography device with an electromagnetic energy (e.g. X-ray) source and detector that is configured to perform fluoroscopy or other real-time radiographic imagery of internal hidden structures of a subject. The name derives from the "C" shaped arm used to position the energy source and energy detector relative to one another such that the portion of the subject to be imaged may be positioned between the source and detector. C-arms may be used for creating radiographs (i.e. still photographs), or more commonly for fluoroscopy.

A C-arm is also sometimes referred to as an "imaging scanner intensifier" although it is perhaps more accurate to think of a C-arm as using an image intensifier. In general, an X-Ray Image Intensifier (XRII) is an image intensifier that converts x-rays into visible light at higher intensity than mere fluorescent screens generally can. C-arm systems generally implement X-ray imaging systems that use such intensifiers (like modern fluoroscopes) to allow converting low-intensity x-rays to a visible output that is easy for human viewing. This intensifying effect allows a viewer to see the structure of the imaged object more easily than would be possible with fluorescent screens alone. The XRII requires lower absorbed doses due to more efficient conversion of x-ray quanta to visible light.

In another example, a C-arm may use a Flat Panel Detector (FDP). FDPs generally refer to a class of solid-state x-ray digital radiography devices similar in principle to the image sensors used in digital photography and video. They are used in both projectional radiography and as an alternative to x-ray image intensifiers (IIs) in fluoroscopy equipment. FDPs include direct and indirect detectors. FDPs are generally more sensitive and faster than radiographic film, thus allowing lower doses of X-ray radiation for a given picture quality. In the case of fluoroscopy, they may be lighter, more durable, smaller, more accurate, and capable of imaging with less distortion than XRII devices.

"Collimator" generally refers to a device that narrows, focuses, or aligns a beam of particles or waves. To narrow can mean either to cause the directions of motion to become more aligned in a specific direction (i.e., make collimated light or parallel rays), or to cause the spatial cross section of the beam to become smaller (i.e. a beam limiting device).

In optics, a collimator may consist of a curved mirror or lens with a light source and/or an image at its focus. This can be used to replicate a target focused at infinity with little or no parallax. Optical collimators can be used to calibrate other optical devices, to check if all elements are aligned on the optical axis, to set elements at proper focus, or to align two or more devices such as binoculars or gun barrels and gunsights. A surveying camera may be collimated by setting its fiduciary markers so that they define the principal point, as in photogrammetry.

In high-energy radiation applications such as X-ray, gamma ray, and neutron optics, a collimator may filter a stream of rays so that only those traveling parallel to a specified direction are allowed through. Collimators are often used for X-ray, gamma-ray, and neutron imaging because traditional lenses typically cannot focus these types of radiation into an image, as is routine with electromagnetic radiation at optical or near-optical wavelengths.

"Computer" generally refers to any computing device configured to compute a result from any number of input values or variables. A computer may include a processor for performing calculations to process input or output. A computer may include a memory for storing values to be processed by the processor, or for storing the results of previous processing.

A computer may also be configured to accept input and output from a wide array of input and output devices for receiving or sending values. Such devices include other computers, keyboards, mice, visual displays, printers, industrial equipment, and systems or machinery of all types and sizes. For example, a computer can control a network interface to perform various network communications upon request. The network interface may be part of the computer, or characterized as separate and remote from the computer.

A computer may be a single, physical, computing device such as a desktop computer, a laptop computer, or may be composed of multiple devices of the same type such as a group of servers operating as one device in a networked cluster, or a heterogeneous combination of different computing devices operating as one computer and linked together by a communication network. The communication network connected to the computer may also be connected to a wider network such as the internet. Thus computer may include one or more physical processors or other computing devices or circuitry, and may also include any suitable type of memory.

A computer may also be a virtual computing platform having an unknown or fluctuating number of physical processors and memories or memory devices. A computer may thus be physically located in one geographical location or physically spread across several widely scattered locations with multiple processors linked together by a communication network to operate as a single computer.

The concept of "computer" and "processor" within a computer or computing device also encompasses any such processor or computing device serving to make calculations or comparisons as part of disclosed system. Processing operations related to threshold comparisons, rules comparisons, calculations, and the like occurring in a computer may occur, for example, on separate servers, the same server with separate processors, or on a virtual computing environment having an unknown number of physical processors as described above.

A computer may be optionally coupled to one or more visual displays and/or may include an integrated visual display. Likewise, displays may be of the same type, or a heterogeneous combination of different visual devices. A computer may also include one or more operator input devices such as a keyboard, mouse, touch screen, laser or infrared pointing device, or gyroscopic pointing device to name just a few representative examples. Also, besides a display, one or more other output devices may be included such as a printer, plotter, industrial manufacturing machine, 3D printer, and the like. As such, various display, input and output device arrangements are possible.

Multiple computers or computing devices may be configured to communicate with one another or with other devices over wired or wireless communication links to form a communication network. Network communications may pass through various computers operating as network appliances such as switches, routers, firewalls or other network devices or interfaces before passing over other larger computer networks such as the internet.

Communications can also be passed over the communication network as wireless data transmissions carried over electromagnetic waves through transmission lines or free space. Such communications include using WiFi or other Wireless Local Area Network (WLAN) or a cellular transmitter/receiver to transfer data. Such signals conform to any of a number of wireless or mobile telecommunications technology standards such as 802.11a/b/g/n, 3G, 4G, and the like.

"Communication Link" generally refers to a connection between two or more communicating entities and may or may not include a communications channel between the communicating entities. The communication between the communicating entities may occur by any suitable means. For example the connection may be implemented as an actual physical link, an electrical link, an electromagnetic link, a logical link, or any other suitable linkage facilitating communication.

In the case of an actual physical link, communication may occur by multiple components in the communication link figured to respond to one another by physical movement of one element in relation to another. In the case of an electrical link, the communication link may be composed of multiple electrical conductors electrically connected to form the communication link.

In the case of an electromagnetic link, elements the connection may be implemented by sending or receiving electromagnetic energy at any suitable frequency, thus allowing communications to pass as electromagnetic waves. These electromagnetic waves may or may not pass through a physical medium such as an optical fiber, or through free space, or any combination thereof. Electromagnetic waves may be passed at any suitable frequency including any frequency in the electromagnetic spectrum.

In the case of a logical link, the communication link may be a conceptual linkage between the sender and recipient such as a transmission station in the receiving station. Logical link may include any combination of physical, electrical, electromagnetic, or other types of communication links.

"Electrically Connected" generally refers to a configuration of two objects that allows electricity to flow between them or through them. In one example, two conductive materials are physically adjacent one another and are sufficiently close together so that electricity can pass between them. In another example, two conductive materials are in physical contact allowing electricity to flow between them.

"Electromagnet Radiation" or "Radiation" generally refers to energy radiated by electromagnetic waves at any frequency or wavelength within the electromagnetic spectrum. Electromagnetic radiation is produced from other types of energy, and is converted to other types when it is destroyed. Electromagnetic radiation carries this energy as it travels moving away from its source at the speed of light (in a vacuum). Electromagnetic radiation also carries both momentum and angular momentum. These properties may all be imparted to matter with which the electromagnetic radiation interacts as it moves outwardly away from its source.

Electromagnetic radiation changes speed as it passes from one medium to another. When transitioning from one media to the next, the physical properties of the new medium can cause some or all of the radiated energy to be reflected while the remaining energy passes into the new medium. This occurs at every junction between media that electromagnetic radiation encounters as it travels.

The photon is the quantum of the electromagnetic interaction, and is the basic constituent of all forms of electromagnetic radiation. The quantum nature of light becomes more apparent at high frequencies as electromagnetic radiation behaves more like particles and less like waves as its frequency increases.

"Electromagnetic Spectrum" generally refers to the range of all possible frequencies of electromagnetic radiation. The electromagnetic spectrum is generally categorized as follows, in order of increasing frequency and energy and decreasing wavelength:

"Extremely low frequency" (ELF) generally designates a band of frequencies from about 3 to about 30 Hz with wavelengths from about 100,000 to 10,000 km long.

"Super low frequency" (SLF) generally designates a band of frequencies generally ranging between about 30 Hz to about 300 Hz with wavelengths of about 10,000 to about 1000 km long.

"Voice frequency" or "voice band" generally designates electromagnetic energy that is audibles to the human ear. Adult males generally speak in the range between about 85 and about 180 Hz while adult females generally converse in the range from about 165 to about 255 Hz.

"Very low frequency" (VLF) generally designates the band of frequencies from about 3 kHz to about 30 kHz with corresponding wavelengths from about 10 to about 100 km long.

"Low-frequency" (LF) generally designates the band of frequencies in the range of about 30 kHz to about 300 kHz with wavelengths range from about 1 to about 10 km.

"Medium frequency" (MF) generally designates the band of frequencies from about 300 kHz to about 3 MHz with wavelengths from about 1000 to about 100 m long.

"High frequency" (HF) generally designates the band of frequencies from about 3 MHz to about 30 MHz having wavelengths from about 100 m to about 10 m long.

"Very high frequency" (VHF) generally designates the band of frequencies from about 30 Hz to about 300 MHz with wavelengths from about 10 m to about 1 m long.

"Ultra high frequency" (UHF) generally designates the band of frequencies from about 300 MHz to about 3 GHz with weight wavelengths ranging from about 1 m to about 10 cm long.

"Super high frequency" (SHF) generally designates the band of frequencies from about 3 GHz to about 30 GHz with wavelengths ranging from about 10 cm to about 1 cm long.

"Extremely high frequency" (EHF) generally designates the band of frequencies from about 30 GHz to about 300 GHz with wavelengths ranging from about 1 cm to about 1 mm long.

"Far infrared" (FIR) generally designates a band of frequencies from about 300 GHz to about 20 THz with wavelengths ranging from about 1 mm to about 15 µm long.

"Long-wavelength infrared" (LWIR) generally designates a band of frequencies from about 20 THz to about 37 THz with wavelengths ranging from about 15 µm to about 8 µm long.

"Mid infrared" (MIR) generally designates a band of frequencies from about 37 THz to about 100 THz with wavelengths from about 8 µm to about 3 µm long.

"Short wavelength infrared" (SWIR) generally designates a band of frequencies from about 100 THz to about 214 THz with wavelengths from about 3 µm to about 1.4 µm long "Near-infrared" (NIR) generally designates a band of frequencies from about 214 THz to about 400 THz with wavelengths from about 1.4 µm to about 750 nm long.

"Visible light" generally designates a band of frequencies from about 400 THz to about 750 THz with wavelengths from about 750 nm to about 400 nm long.

"Near ultraviolet" (NUV) generally designates a band of frequencies from about 750 THz to about 1 PHz with wavelengths from about 400 nm to about 300 nm long.

"Middle ultraviolet" (MUV) generally designates a band of frequencies from about 1 PHz to about 1.5 PHz with wavelengths from about 300 nm to about 200 nm long.

"Far ultraviolet" (FUV) generally designates a band of frequencies from about 1.5 PHz to about 2.48 PHz with wavelengths from about 200 nm to about 122 nm long.

"Extreme ultraviolet" (EUV) generally designates a band of frequencies from about 2.48 PHz to about 30 PHz with wavelengths from about 121 nm to about 10 nm long.

"Soft x-rays" (SX) generally designates a band of frequencies from about 30 PHz to about 3 EHz with wavelengths from about 10 nm to about 100 pm long.

"Hard x-rays" (HX) generally designates a band of frequencies from about 3 EHz to about 30 EHz with wavelengths from about 100 pm to about 10 pm long.

"Gamma rays" generally designates a band of frequencies above about 30 EHz with wavelengths less than about 10 pm long.

"Electromagnetic Waves" generally refers to waves having a separate electrical and a magnetic component. The electrical and magnetic components of an electromagnetic wave oscillate in phase and are always separated by a 90 degree angle. Electromagnetic waves can radiate from a source to create electromagnetic radiation capable of passing through a medium or through a vacuum. Electromagnetic waves include waves oscillating at any frequency in the electromagnetic spectrum including, but not limited to, radio waves, visible and invisible light, X-rays, and gamma-rays.

"Fluoroscopes" generally refers to an instrument used for viewing images in real time that are created by electromagnetic energy passing through a surface that includes phosphors that glow when struck by the passing rays. In this way, invisible electromagnetic energy may be made visible for viewing in real time as the electromagnetic energy is being transmitted. Thus, invisible radiation becomes visible light.

"Fluoroscopy" generally refers to an imaging technique that uses a device (such as a fluoroscope, or electronic detector) to capture electromagnetic energy passing near or through an object and generate a real-time moving image. In medical imaging, a fluoroscope allows a physician to watch the internal structure and function of a subject as it occurs in real time. This is useful for both diagnosis and therapy and occurs in many areas of medicine. In one example, a fluoroscope consists of an X-ray source and a fluorescent screen, between which a subject is placed. X-ray image intensifiers and cameras may be used as well, to improve the image's visibility and make it available on a remote display screen. An electronic detector, rather than a fluoroscope, may be used to detect the electromagnetic energy and generate a moving image. Although no fluoroscope is used, the procedure may still be referred to as fluoroscopy.

The use of X-rays, a form of ionizing radiation, requires the potential risks from a procedure to be carefully balanced with the benefits of the procedure to the subject. Because the subject must be exposed to a continuous source of X-rays instead of a momentary pulse, a fluoroscopy procedure generally subjects a subject to a higher absorbed dose of radiation than an ordinary (still) radiograph. Only important applications such as health care, bodily safety, food safety, nondestructive testing, and scientific research meet the risk-benefit threshold for use. Fluoroscopy is also used in airport security scanners to check for hidden weapons or bombs. These machines use lower doses of radiation than medical fluoroscopy. The reason for higher doses in medical applications is that they are more demanding about tissue contrast, and for the same reason they sometimes require contrast media.

"Lower segment" generally refers to the distance from the symphysis pubis to the plantar surface of the foot and represents the "limb" contribution to total height. At birth the normal upper to lower segment ratio is 1.7:1. The legs grow more rapidly than the trunk, and by age 10 the segments are equal and remain so in adults.

"Medical imaging application" generally refers to any medical procedure or medical condition for which imaging may be desired. By way of a non-limiting example, medical imaging applications may include interventional pain, general surgery, cardiology, orthopedics, fluoroscopy, or neurosurgery.

"Memory" generally refers to any storage system or device configured to retain data or information. Each memory may include one or more types of solid-state electronic memory, magnetic memory, or optical memory, just to name a few. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, each memory may be volatile, nonvolatile, or a hybrid combination of volatile and nonvolatile varieties.

"Mid-upper arm" generally refers to about the midpoint between the acromial process and the olecranon process. Mid-upper arm circumference may be used to calculate mid-upper arm muscle circumference. Muscle circumferences less than the 30th percentile may suggest severe depletion of protein stores.

"Multiple" as used herein is synonymous with the term "plurality" and refers to more than one, or by extension, two or more.

"Optionally" as used herein means discretionary; not required; possible, but not compulsory; left to personal choice.

"Operating Settings Module" generally refers to software that is able to accept input and to use that input to calculate operating settings for an imaging device to produce a viewable image. The input accepted by the operating settings module may be any data, descriptions, or other form of information that may be used to optimize operating settings for an imaging system. The operating settings module may calculate operating settings using an equation or a set of equations, by comparing input to historical data, or by any other suitable method for determining operating settings that produce a readable image.

"Optical Fiber" generally refers to an electromagnetic waveguide having an elongate conduit that includes a substantially transparent medium through which electromagnetic energy travels as it traverses the long axis of the conduit. Electromagnetic radiation may be maintained within the conduit by total internal reflection of the electromagnetic radiation as it traverses the conduit. Total internal reflection is generally achieved using optical fibers that include a substantially transparent core surrounded by a second substantially transparent cladding material with a lower index of refraction than the core.

Optical fibers are generally constructed of dielectric material that is not electrically conductive but is substantially transparent. Such materials may or may not include any combination of extruded glass such as silica, fluoride glass, phosphate glass, Chalcogenide glass, or polymeric material such as various types of plastic, or other suitable material and may be configured with any suitable cross-sectional shape, length, or dimension. Examples of electromagnetic energy that may be successfully passed through optical fibers include electromagnetic waves in the near-infrared, mid-infrared, and visible light portion of the electromagnetic spectrum, although electromagnetic energy of any suitable frequency may be used.

"Processor" generally refers to one or more electronic components configured to operate as a single unit configured or programmed to process input to generate an output. Alternatively, when of a multi-component form, a processor may have one or more components located remotely relative to the others. One or more components of each processor may be of the electronic variety defining digital circuitry, analog circuitry, or both. In one example, each processor is of a conventional, integrated circuit microprocessor arrangement, such as one or more PENTIUM, i3, i5 or i7 processors supplied by INTEL Corporation of 2200 Mission College Boulevard, Santa Clara, Calif. 95052, USA.

Another example of a processor is an Application-Specific Integrated Circuit (ASIC). An ASIC is an Integrated Circuit (IC) customized to perform a specific series of logical operations is controlling the computer to perform specific tasks or functions. An ASIC is an example of a processor for a special purpose computer, rather than a processor configured for general-purpose use. An application-specific integrated circuit generally is not reprogrammable to perform other functions and may be programmed once when it is manufactured.

In another example, a processor may be of the "field programmable" type. Such processors may be programmed multiple times "in the field" to perform various specialized or general functions after they are manufactured. A field-programmable processor may include a Field-Programmable Gate Array (FPGA) in an integrated circuit in the processor. FPGA may be programmed to perform a specific series of instructions which may be retained in nonvolatile memory cells in the FPGA. The FPGA may be configured by a customer or a designer using a hardware description language (HDL). In FPGA may be reprogrammed using another computer to reconfigure the FPGA to implement a new set of commands or operating instructions. Such an operation may be executed in any suitable means such as by a firmware upgrade to the processor circuitry.

Just as the concept of a computer is not limited to a single physical device in a single location, so also the concept of a "processor" is not limited to a single physical logic circuit or package of circuits but includes one or more such circuits or circuit packages possibly contained within or across multiple computers in numerous physical locations. In a virtual computing environment, an unknown number of physical processors may be actively processing data, the unknown number may automatically change over time as well.

The concept of a "processor" includes a device configured or programmed to make threshold comparisons, rules comparisons, calculations, or perform logical operations applying a rule to data yielding a logical result (e.g. "true" or "false"). Processing activities may occur in multiple single processors on separate servers, on multiple processors in a single server with separate processors, or on multiple processors physically remote from one another in separate computing devices.

"Radiography" generally refers to an imaging technique using electromagnetic waves (e.g. X-rays) to create an image of an object. In one example, radiography is used to view interior structures of an opaque object where a beam of X-rays are produced by an X-ray generator and are projected toward the object. A certain amount of X-ray is absorbed by the object, dependent on its density and structural composition. The X-rays that pass through the object may be captured behind the object by a detector (such as by photographic film or by a digital detector). The generation of flat two dimensional images by this technique is sometimes referred to as "projectional radiography". Computed Tomography (CT) scanning is an example of radiography where multiple two dimensional images from different angles undergo computer processing to generate three dimensional representations.

In another example, an image may be produced by detecting electromagnetic energy that reflects from an object to form an image. This technique may rely on the Compton scattering effect of X-rays, a form of ionizing radiation. Rather than detecting X-rays that have passed through the object, "backscatter X-ray detection" relies primarily on detecting radiation reflected off the object to form an image. The detected backscatter pattern is generally dependent on the material properties of the object and is often used for imaging organic material.

Applications of radiography include medical (or "diagnostic") radiography that includes radiographic photography (still images), and fluoroscopy (real-time imagery) of subjects. Other uses include industrial radiography to determine internal composition of manufactured objects, and airport security where "body scanners" that may use backscatter X-ray detection to create images of passengers.

"Receive" generally refers to accepting something transferred, communicated, conveyed, relayed, dispatched, or forwarded. The concept may or may not include the act of listening or waiting for something to arrive from a transmitting entity. For example, a transmission may be received without knowledge as to who or what transmitted it. Likewise the transmission may be sent with or without knowledge of who or what is receiving it. To "receive" may include, but is not limited to, the act of capturing or obtaining electromagnetic energy at any suitable frequency in the electromagnetic spectrum. Receiving may occur by sensing electromagnetic radiation. Sensing electromagnetic radiation may involve detecting energy waves moving through or from a medium such as a wire or optical fiber. Receiving includes receiving digital signals which may define various types of analog or binary data such as signals, datagrams, packets and the like.

"Skinfold thickness" generally refers to a measure of subcutaneous fat and is used to estimate total adiposity. This measurement may be taken, for example, at the mid-upper arm. Obesity may be indicated by a value greater than 23 mm in men and 30 mm in women. Severe depletion of energy stores may be indicated by values below the 30th percentile.

"Source dose rate" (SDR): generally refers to the dose rate delivered to the subject, which is then the maximum potential dose rate exposure to both the subject and bystanders.

"Source dose scatter" (SDS): is defined as the source dose rate over time and distance from the SDR.

"Transmit" generally refers to causing something to be transferred, communicated, conveyed, relayed, dispatched, or forwarded. The concept may or may not include the act of conveying something from a transmitting entity to a receiving entity. For example, a transmission may be received without knowledge as to who or what transmitted it. Likewise the transmission may be sent with or without knowledge of who or what is receiving it. To "transmit" may include, but is not limited to, the act of sending or broadcasting electromagnetic energy at any suitable frequency in the electromagnetic spectrum. Transmissions may include digital signals which may define various types of binary data such as datagrams, packets and the like. A transmission may also include analog signals.

"Trunk or Upper Segment" generally refers to the distance from the symphysis pubis to the crown of the head.

"User Interface" generally refers an aspect of a device or computer program that provides a means by which the user and a device or computer program interact, in particular by coordinating the use of input devices and software. A user interface may be said to be "graphical" in nature in that the device or software executing on the computer may present images, text, graphics, and the like using a display device to present output meaningful to the user, and accept input from the user in conjunction with the graphical display of the output. In another example, a user interface may include lights, LEDs, 7-segment displays, LCD displays, physical buttons, switches, levers, or other devices for providing output to a user and accepting input.

What is claimed is:
1. A system comprising:
an imaging device configured to capture an image of a subject using electromagnetic radiation, the imaging device defining operating settings for controlling behavior of the imaging device; and
control logic configured to:
receive, from a user device, subject data corresponding to the subject;
automatically determine the operating settings based on:
a specific type of imaging procedure to be performed,
a target location of the subject, and
the subject data, wherein the operating settings comprise one or more of:
peak kilovoltage,
tube current, or
exposure time; and
transmit the operating settings to the imaging device,
wherein the imaging device is further configured to, in response to receiving the operating settings from the control logic, generate an image of the subject using the operating settings and deactivate an automatic exposure control setting of the imaging device prior to generating the image.

2. The system of claim 1, comprising:
a computer remote from the imaging device; and
a communication link between the imaging device and the computer,
wherein the control logic is in the computer, and wherein the operating settings are transmitted from the computer to the imaging device using a communication link electrically connecting the computer to the imaging device.

3. The system of claim 2, wherein the computer has a user interface that is configured to accept input defining the operating settings, and wherein the input includes:
information identifying the imaging device;
the specific type of imaging procedure to be performed by the imaging device;
the target location of the subject which is to be imaged by the imaging device; and
the subject data, wherein the subject data includes subject gender, subject body type, and subject weight.

4. The system of claim 2, wherein the communication link includes a wire electrically connecting the computer to the imaging device.

5. The system of claim 2, wherein the communication link includes a wireless connection electrically connecting the computer to the imaging device.

6. The system of claim 1, comprising:
a first and a second computer, both remote from the imaging device;
a first communication link between the imaging device and the first computer; and
a second communication link between the first computer and the second computer,
wherein the control logic is in the second computer, wherein the operating settings are transmitted from the second computer to the first computer using the second communication link, and wherein the operating settings are transmitted from the first computer to the imaging device using the first communication link.

7. The system of claim 1, comprising:
a controller configured to activate and deactivate the imaging device,
wherein the control logic is in the controller, and wherein the controller is mounted in a housing of the imaging device and is configured to control the imaging device to generate an image of the subject using the calculated operating settings.

8. The system of claim 7, comprising:
a computer remote from the imaging device; and
a communication link between the controller and the computer,
wherein the operating settings are transmitted from the computer to the controller using a communication link electrically connecting the computer to the controller.

9. The system of claim 8, comprising:
an imaging system user interface of the imaging device that is arranged and configured to accept input defining the operating settings, or any combination thereof;
wherein the controller is arranged and configured to automatically accept input from the imaging system user interface and send it to the computer; and
wherein the controller is arranged and configured to automatically accept input from the computer and adjust the user interface and the operating settings of the imaging device accordingly.

10. The system of claim 1, comprising:
a computer remote from the imaging device;
a controller configured to activate and deactivate the imaging device; and a communication link between the controller and the computer;
wherein the control logic is in the computer and the controller is responsive to accept operating settings from the computer; and
wherein the controller is mounted in a housing of the imaging device and is configured to control the imaging device to generate an image of the subject using the operating settings.

11. The system of claim 10, comprising:
an imaging system user interface of the imaging device configured to accept input defining the operating settings, wherein the controller is responsive to the imaging system user interface, and wherein the controller is configured to send the operating settings received from the imaging system user interface to the computer using the communications link.

12. The system of claim 11, comprising:
a computer user interface of the computer configured to accept input defining the operating settings, wherein the computer is configured to send the operating settings from the computer user interface to the controller using the communications link.

13. The system of claim 1, wherein the operating settings include information identifying the imaging device.

14. The system of claim 1, wherein the at least one physical characteristic of the subject includes any of subject gender, subject body type, and subject weight, or any combination thereof.

15. The system of claim 1, wherein the imaging device generates the image by generating x-ray radiation, wherein the x-ray radiation is generated for a period of time about equal to the exposure time, and where the exposure time is less than 1 second.

16. The system of claim 1, wherein an exposure time required to generate an image is less than about 1 second.

17. The system of claim 1, wherein an exposure time required to generate an image is less than about 0.6 seconds.

18. The system of claim 1, wherein a Scatter Rate of the imaging device when activated is less than about 300 mR/hour within 4 feet of the imaging device.

19. The system of claim 1, wherein a Scatter Rate of the imaging device when activated is less than about 150 mR/hour within 4 feet of the imaging device.

20. A method comprising:
receiving, by control logic and from a user device, subject data corresponding to a subject to be imaged by an imaging device, wherein the imaging device is configured to capture an image of a subject using electromagnetic radiation and based on operating settings that control behavior of the imaging device;
automatically determining, by the control logic, the operating settings based on:
a specific type of imaging procedure to be performed,
a target location of the subject, and
the subject data, wherein the operating settings comprise one or more of:
  peak kilovoltage,
  tube current, or
  exposure time;
transmitting the operating settings to the imaging device, wherein the imaging device is configured to, in response to receiving the operating settings from the control logic, generate an image of the subject using the operating settings and deactivating an automatic exposure control setting of the imaging device prior to generating the image.

* * * * *